United States Patent
Davies et al.

(10) Patent No.: US 11,684,447 B2
(45) Date of Patent: *Jun. 27, 2023

(54) RADIOFREQUENCY PERFORATION APPARATUS

(71) Applicant: Boston Scientific Medical Device Limited, Ballybrit (IE)

(72) Inventors: Gareth Davies, Toronto (CA); John Paul Urbanski, Toronto (CA)

(73) Assignee: Boston Scientific Medical Device Limited, Galway (IE)

(*) Notice: Subject to any disclaimer, the term of this patent is extended or adjusted under 35 U.S.C. 154(b) by 228 days.

This patent is subject to a terminal disclaimer.

(21) Appl. No.: 17/130,691

(22) Filed: Dec. 22, 2020

(65) Prior Publication Data

US 2021/0106400 A1  Apr. 15, 2021

Related U.S. Application Data

(63) Continuation of application No. 14/404,518, filed as application No. PCT/IB2012/056315 on Nov. 9, 2012, now Pat. No. 10,898,291.

(Continued)

(51) Int. Cl.
*A61B 18/14* (2006.01)
*A61B 90/00* (2016.01)
(Continued)

(52) U.S. Cl.
CPC ............. *A61B 90/39* (2016.02); *A61B 5/064* (2013.01); *A61B 18/1492* (2013.01);
(Continued)

(58) Field of Classification Search
CPC ........... A61B 18/1492; A61B 18/1482; A61B 2018/00351–00392; A61B 5/065;
(Continued)

(56) References Cited

U.S. PATENT DOCUMENTS 175,254 A   3/1876 Oberly
827,626 A   7/1906 Gillet
(Continued)

FOREIGN PATENT DOCUMENTS

EP   0513836 A1  11/1992
JP   S5996036    6/1984
(Continued)

OTHER PUBLICATIONS

Japanese Office Action from corresponding JPO application 2021-126774, dated Jun. 29, 2022, Japan Patent Office, 5 pages.
(Continued)

*Primary Examiner* — Joanne M Rodden
*Assistant Examiner* — Sean W Collins
(74) *Attorney, Agent, or Firm* — Nelson Mullins Riley & Scarborough LLP

(57) ABSTRACT

Medical devices are disclosed having improved visualization of a portion of the medical device insertable into a patient's body while minimizing obstruction of fluid flow through a lumen of the device and while minimizing an increase in the outer diameter of the device attributable to the feature providing improved visualization. The device can include, for example, an imaging marker distal to lumen openings (exit ports), or, where the device comprises a tube, such as a metallic tube, an imaging marker embedded into a wall of the tube. Another embodiment includes attaching a marker to the surface on the inside of a lumen of a medical device without embedding the marker. Various alternative embodiments, methods and applications of using such devices are disclosed as well.

19 Claims, 18 Drawing Sheets

Related U.S. Application Data

(60) Provisional application No. 61/653,967, filed on May 31, 2012.

(51) Int. Cl.
*A61M 25/01* (2006.01)
*A61B 5/06* (2006.01)
*A61B 18/00* (2006.01)

(52) U.S. Cl.
CPC .... *A61M 25/0108* (2013.01); *A61M 25/0127* (2013.01); *A61B 90/37* (2016.02); *A61B 2018/00077* (2013.01); *A61B 2018/1412* (2013.01); *A61B 2090/3925* (2016.02); *A61B 2090/3954* (2016.02); *A61B 2090/3966* (2016.02); *A61B 2217/005* (2013.01); *A61B 2217/007* (2013.01); *A61B 2218/002* (2013.01)

(58) Field of Classification Search
CPC .. A61B 90/39; A61B 2090/3904–3945; A61B 2090/3954; A61B 2090/3958; A61B 2090/3966–3983; A61B 2090/3995; A61B 2218/001–008

See application file for complete search history.

(56) References Cited

U.S. PATENT DOCUMENTS

| | | |
|---|---|---|
| 848,711 A | 4/1907 | Daniel |
| 1,072,954 A | 9/1913 | Junn |
| 1,279,654 A | 9/1918 | Charlesworth |
| 1,918,094 A | 7/1933 | Geekas |
| 1,996,986 A | 4/1935 | Weinberg |
| 2,021,989 A | 11/1935 | De Master |
| 2,146,636 A | 2/1939 | Lipchow |
| 3,429,574 A | 2/1969 | Williams |
| 3,448,739 A | 6/1969 | Stark et al. |
| 3,575,415 A | 4/1971 | Fulp et al. |
| 3,595,239 A | 7/1971 | Petersen |
| 4,029,102 A | 6/1977 | Barger |
| 4,129,129 A | 12/1978 | Amrine |
| 4,244,362 A | 1/1981 | Anderson |
| 4,401,124 A | 8/1983 | Guess et al. |
| 4,577,637 A | 3/1986 | Mueller, Jr. |
| 4,639,252 A | 1/1987 | Kelly et al. |
| 4,641,649 A | 2/1987 | Walinsky et al. |
| 4,669,467 A | 6/1987 | Willett et al. |
| 4,682,596 A | 7/1987 | Bales et al. |
| 4,790,311 A | 12/1988 | Ruiz |
| 4,790,809 A | 12/1988 | Kuntz |
| 4,793,350 A | 12/1988 | Mar et al. |
| 4,807,620 A | 2/1989 | Strul et al. |
| 4,832,048 A | 5/1989 | Cohen |
| 4,840,622 A | 6/1989 | Hardy |
| 4,863,441 A | 9/1989 | Lindsay et al. |
| 4,884,567 A | 12/1989 | Elliott et al. |
| 4,892,104 A | 1/1990 | Ito et al. |
| 4,896,671 A | 1/1990 | Cunningham et al. |
| 4,928,693 A | 5/1990 | Goodin et al. |
| 4,936,281 A | 6/1990 | Stasz |
| 4,960,410 A | 10/1990 | Pinchuk |
| 4,977,897 A | 12/1990 | Hurwitz |
| 4,998,933 A | 3/1991 | Eggers et al. |
| 5,006,119 A | 4/1991 | Acker et al. |
| 5,019,076 A | 5/1991 | Yamanashi et al. |
| 5,047,026 A | 9/1991 | Rydell |
| 5,081,997 A | 1/1992 | Bosley et al. |
| 5,097,843 A | 3/1992 | Soukup et al. |
| 5,098,431 A | 3/1992 | Rydell |
| 5,112,048 A | 5/1992 | Kienle |
| 5,154,724 A | 10/1992 | Andrews |
| 5,201,756 A | 4/1993 | Horzewski et al. |
| 5,209,741 A | 5/1993 | Spaeth |
| 5,211,183 A | 5/1993 | Wilson |
| 5,221,256 A | 6/1993 | Mahurkar |
| 5,230,349 A | 7/1993 | Langberg |
| 5,281,216 A | 1/1994 | Klicek |
| 5,300,068 A | 4/1994 | Rosar et al. |
| 5,300,069 A | 4/1994 | Hunsberger et al. |
| 5,314,418 A | 5/1994 | Takano et al. |
| 5,318,525 A | 6/1994 | West et al. |
| 5,327,905 A | 7/1994 | Avitall |
| 5,364,393 A | 11/1994 | Auth et al. |
| 5,372,596 A | 12/1994 | Klicek et al. |
| 5,380,304 A | 1/1995 | Parker |
| 5,397,304 A | 3/1995 | Truckai |
| 5,403,338 A | 4/1995 | Milo |
| 5,406,960 A | 4/1995 | Corso, Jr. |
| 5,423,809 A | 6/1995 | Klicek |
| 5,425,382 A | 6/1995 | Golden et al. |
| 5,485,667 A | 1/1996 | Kleshinski |
| 5,488,959 A | 2/1996 | Ales |
| 5,489,277 A | 2/1996 | Tolkoff et al. |
| 5,490,859 A | 2/1996 | Mische et al. |
| 5,497,774 A | 3/1996 | Swartz et al. |
| 5,507,751 A | 4/1996 | Goode et al. |
| 5,509,411 A | 4/1996 | Littmann et al. |
| 5,540,681 A | 7/1996 | Strul et al. |
| 5,545,200 A | 8/1996 | West et al. |
| 5,555,618 A | 9/1996 | Winkler |
| 5,571,088 A | 11/1996 | Lennox et al. |
| 5,575,766 A | 11/1996 | Swartz et al. |
| 5,575,772 A | 11/1996 | Lennox |
| 5,599,347 A | 2/1997 | Hart et al. |
| 5,605,162 A | 2/1997 | Mirzaee et al. |
| 5,617,878 A | 4/1997 | Taheri |
| 5,622,169 A | 4/1997 | Golden et al. |
| 5,624,430 A | 4/1997 | Eton et al. |
| 5,640,970 A | 6/1997 | Arenas |
| 5,667,488 A | 9/1997 | Lundquist et al. |
| 5,673,695 A | 10/1997 | McGee et al. |
| 5,674,208 A | 10/1997 | Berg et al. |
| 5,683,366 A | 11/1997 | Eggers et al. |
| 5,720,744 A | 2/1998 | Eggleston et al. |
| 5,741,249 A | 4/1998 | Moss et al. |
| 5,766,135 A | 6/1998 | Terwilliger |
| 5,779,688 A | 7/1998 | Imran et al. |
| 5,810,764 A | 9/1998 | Eggers et al. |
| 5,814,028 A | 9/1998 | Swartz et al. |
| 5,830,214 A | 11/1998 | Flom et al. |
| 5,836,875 A | 11/1998 | Webster, Jr. |
| 5,849,011 A | 12/1998 | Jones et al. |
| 5,851,210 A | 12/1998 | Torossian |
| 5,885,227 A | 3/1999 | Finlayson |
| 5,888,201 A | 3/1999 | Stinson et al. |
| 5,893,848 A | 4/1999 | Negus et al. |
| 5,893,885 A | 4/1999 | Webster, Jr. |
| 5,904,679 A | 5/1999 | Clayman |
| 5,916,210 A | 6/1999 | Winston |
| 5,919,188 A | 7/1999 | Shearon et al. |
| 5,921,957 A | 7/1999 | Killion et al. |
| 5,921,978 A | 7/1999 | Thompson et al. |
| 5,931,818 A | 8/1999 | Werp et al. |
| 5,944,023 A | 8/1999 | Johnson et al. |
| 5,951,482 A | 9/1999 | Winston et al. |
| 5,957,842 A | 9/1999 | Littmann et al. |
| 5,964,757 A | 10/1999 | Ponzi |
| 5,967,976 A | 10/1999 | Larsen et al. |
| 5,989,276 A | 11/1999 | Houser et al. |
| 6,007,555 A | 12/1999 | Devine |
| 6,009,877 A | 1/2000 | Edwards |
| 6,013,072 A | 1/2000 | Winston et al. |
| 6,017,340 A | 1/2000 | Cassidy et al. |
| 6,018,676 A | 1/2000 | Davis et al. |
| 6,030,380 A | 2/2000 | Auth et al. |
| 6,032,674 A | 3/2000 | Eggers et al. |
| 6,048,349 A | 4/2000 | Winston et al. |
| 6,053,870 A | 4/2000 | Fulton, III |
| 6,053,904 A | 4/2000 | Scribner et al. |
| 6,056,747 A | 5/2000 | Saadat et al. |
| 6,063,093 A | 5/2000 | Winston et al. |
| 6,093,185 A | 7/2000 | Ellis et al. |
| 6,106,515 A | 8/2000 | Winston et al. |

(56) References Cited

U.S. PATENT DOCUMENTS

| | | |
|---|---|---|
| 6,106,520 A | 8/2000 | Laufer et al. |
| 6,117,131 A | 9/2000 | Taylor |
| 6,142,992 A | 11/2000 | Cheng et al. |
| 6,146,380 A | 11/2000 | Racz et al. |
| 6,155,264 A | 12/2000 | Ressemann et al. |
| 6,156,031 A | 12/2000 | Aita et al. |
| 6,171,305 B1 | 1/2001 | Sherman |
| 6,179,824 B1 | 1/2001 | Eggers et al. |
| 6,193,676 B1 | 2/2001 | Winston et al. |
| 6,193,715 B1 | 2/2001 | Wrublewski et al. |
| 6,210,408 B1 | 4/2001 | Chandrasekaran et al. |
| 6,217,575 B1 | 4/2001 | Devore et al. |
| 6,221,061 B1 | 4/2001 | Engelson et al. |
| 6,228,076 B1 | 5/2001 | Winston et al. |
| 6,245,054 B1 | 6/2001 | Fuimaono et al. |
| 6,267,758 B1 | 7/2001 | Daw et al. |
| 6,283,983 B1 | 9/2001 | Makower et al. |
| 6,285,903 B1 | 9/2001 | Rosenthal et al. |
| 6,292,678 B1 | 9/2001 | Hall et al. |
| 6,293,945 B1 | 9/2001 | Parins et al. |
| 6,296,615 B1 | 10/2001 | Brockway et al. |
| 6,296,636 B1 | 10/2001 | Cheng et al. |
| 6,302,898 B1 | 10/2001 | Edwards et al. |
| 6,304,769 B1 | 10/2001 | Arenson et al. |
| 6,315,777 B1 | 11/2001 | Comben |
| 6,328,699 B1 | 12/2001 | Eigler et al. |
| 6,360,128 B2 | 3/2002 | Kordis et al. |
| 6,364,877 B1 | 4/2002 | Goble et al. |
| 6,385,472 B1 | 5/2002 | Hall et al. |
| 6,394,976 B1 | 5/2002 | Winston et al. |
| 6,395,002 B1 | 5/2002 | Ellman et al. |
| 6,402,740 B1 | 6/2002 | Ellis et al. |
| 6,419,674 B1 | 7/2002 | Bowser et al. |
| 6,428,551 B1 | 8/2002 | Hall et al. |
| 6,450,989 B2 | 9/2002 | Dubrul |
| 6,475,214 B1 | 11/2002 | Moaddeb |
| 6,485,485 B1 | 11/2002 | Winston et al. |
| 6,501,992 B1 | 12/2002 | Belden et al. |
| 6,508,754 B1 | 1/2003 | Liprie et al. |
| 6,520,934 B1 | 2/2003 | Lee et al. |
| 6,524,303 B1 | 2/2003 | Garibaldi |
| 6,530,923 B1 | 3/2003 | Dubrul |
| 6,554,827 B2 | 4/2003 | Chandrasekaran et al. |
| 6,562,031 B2 | 5/2003 | Chandrasekaran et al. |
| 6,562,049 B1 | 5/2003 | Norlander et al. |
| 6,565,562 B1 | 5/2003 | Shah et al. |
| 6,607,529 B1 | 8/2003 | Jones et al. |
| 6,632,227 B2 | 10/2003 | Edwards et al. |
| 6,639,999 B1 | 10/2003 | Cookingham et al. |
| 6,650,923 B1 | 11/2003 | Lesh et al. |
| 6,651,672 B2 | 11/2003 | Roth |
| 6,662,034 B2 | 12/2003 | Segner et al. |
| 6,663,621 B1 | 12/2003 | Winston et al. |
| 6,702,811 B2 | 3/2004 | Stewart et al. |
| 6,709,444 B1 | 3/2004 | Makower |
| 6,723,052 B2 | 4/2004 | Mills |
| 6,733,511 B2 | 5/2004 | Hall et al. |
| 6,740,103 B2 | 5/2004 | Hall et al. |
| 6,752,800 B1 | 6/2004 | Winston et al. |
| 6,755,816 B2 | 6/2004 | Ritter et al. |
| 6,811,544 B2 | 11/2004 | Schaer |
| 6,814,733 B2 | 11/2004 | Schwartz et al. |
| 6,820,614 B2 | 11/2004 | Bonutti |
| 6,832,715 B2 | 12/2004 | Eungard et al. |
| 6,834,201 B2 | 12/2004 | Gillies et al. |
| 6,842,639 B1 | 1/2005 | Winston et al. |
| 6,852,109 B2 | 2/2005 | Winston et al. |
| 6,855,143 B2 | 2/2005 | Davison et al. |
| 6,860,856 B2 | 3/2005 | Ward et al. |
| 6,869,431 B2 | 3/2005 | Maguire et al. |
| 6,911,026 B1 | 6/2005 | Hall et al. |
| 6,951,554 B2 | 10/2005 | Johansen et al. |
| 6,951,555 B1 | 10/2005 | Suresh et al. |
| 6,955,675 B2 | 10/2005 | Jain |
| 6,970,732 B2 | 11/2005 | Winston et al. |
| 6,980,843 B2 | 12/2005 | Eng et al. |
| 7,029,470 B2 | 4/2006 | Francischelli et al. |
| 7,056,294 B2 | 6/2006 | Khairkhahan et al. |
| 7,083,566 B2 | 8/2006 | Tornes et al. |
| 7,112,197 B2 | 9/2006 | Hartley et al. |
| 7,169,118 B2 | 1/2007 | Reynolds et al. |
| 7,277,762 B2 | 10/2007 | Belden et al. |
| 7,335,197 B2 | 2/2008 | Sage et al. |
| 7,618,430 B2 | 11/2009 | Scheib |
| 7,651,492 B2 | 1/2010 | Wham |
| 7,666,203 B2 | 2/2010 | Chanduszko et al. |
| 7,678,081 B2 | 3/2010 | Whiting et al. |
| 7,682,360 B2 | 3/2010 | Guerra |
| 7,828,796 B2 | 11/2010 | Wong et al. |
| 7,862,563 B1 * | 1/2011 | Cosman ............ A61B 18/1477 606/49 |
| 7,900,928 B2 | 3/2011 | Held et al. |
| 7,925,358 B2 | 4/2011 | Belden et al. |
| 8,192,425 B2 | 6/2012 | Mirza et al. |
| 8,257,323 B2 | 9/2012 | Joseph et al. |
| 8,388,549 B2 | 3/2013 | Paul et al. |
| 8,500,697 B2 | 8/2013 | Kurth et al. |
| 10,898,291 B2 * | 1/2021 | Davies ............ A61M 25/0127 |
| 11,339,579 B1 | 5/2022 | Stearns |
| 2001/0012934 A1 | 8/2001 | Chandrasekaran et al. |
| 2001/0021867 A1 | 9/2001 | Kordis et al. |
| 2002/0019644 A1 | 2/2002 | Hastings et al. |
| 2002/0022781 A1 | 2/2002 | McIntire et al. |
| 2002/0022836 A1 | 2/2002 | Goble et al. |
| 2002/0035361 A1 | 3/2002 | Houser et al. |
| 2002/0087153 A1 | 7/2002 | Roschak et al. |
| 2002/0087156 A1 | 7/2002 | Maguire et al. |
| 2002/0095148 A1 | 7/2002 | Kinsella et al. |
| 2002/0111618 A1 | 8/2002 | Stewart et al. |
| 2002/0120259 A1 | 8/2002 | Lettice et al. |
| 2002/0123749 A1 | 9/2002 | Jain |
| 2002/0147485 A1 | 10/2002 | Mamo et al. |
| 2002/0169377 A1 | 11/2002 | Khairkhahan et al. |
| 2002/0188302 A1 | 12/2002 | Berg et al. |
| 2002/0198521 A1 | 12/2002 | Maguire |
| 2003/0032929 A1 | 2/2003 | McGuckin |
| 2003/0040742 A1 | 2/2003 | Underwood et al. |
| 2003/0144658 A1 | 7/2003 | Schwartz et al. |
| 2003/0158480 A1 | 8/2003 | Tornes et al. |
| 2003/0163153 A1 | 8/2003 | Scheib |
| 2003/0225392 A1 | 12/2003 | McMichael et al. |
| 2004/0015162 A1 | 1/2004 | McGaffigan |
| 2004/0024396 A1 | 2/2004 | Eggers |
| 2004/0030328 A1 | 2/2004 | Eggers et al. |
| 2004/0044350 A1 | 3/2004 | Martin et al. |
| 2004/0073243 A1 | 4/2004 | Sepetka et al. |
| 2004/0077948 A1 | 4/2004 | Violante et al. |
| 2004/0101564 A1 | 5/2004 | Rioux et al. |
| 2004/0116851 A1 | 6/2004 | Johansen et al. |
| 2004/0127963 A1 | 7/2004 | Uchida et al. |
| 2004/0133113 A1 | 7/2004 | Krishnan |
| 2004/0133130 A1 | 7/2004 | Ferry et al. |
| 2004/0143256 A1 | 7/2004 | Bednarek |
| 2004/0143261 A1 | 7/2004 | Hartley et al. |
| 2004/0143262 A1 | 7/2004 | Visram et al. |
| 2004/0147950 A1 | 7/2004 | Mueller et al. |
| 2004/0167436 A1 * | 8/2004 | Reynolds ............ A61M 25/09 600/585 |
| 2004/0181213 A1 | 9/2004 | Gondo |
| 2004/0230188 A1 | 11/2004 | Cioanta et al. |
| 2005/0004585 A1 | 1/2005 | Hall et al. |
| 2005/0010208 A1 | 1/2005 | Winston et al. |
| 2005/0049628 A1 | 3/2005 | Schweikert et al. |
| 2005/0059966 A1 | 3/2005 | McClurken et al. |
| 2005/0065507 A1 | 3/2005 | Hartley et al. |
| 2005/0080410 A1 | 4/2005 | Rioux et al. |
| 2005/0085806 A1 | 4/2005 | Auge et al. |
| 2005/0096529 A1 | 5/2005 | Cooper et al. |
| 2005/0101984 A1 | 5/2005 | Chanduszko et al. |
| 2005/0119556 A1 | 6/2005 | Gillies et al. |
| 2005/0137527 A1 | 6/2005 | Kunin |
| 2005/0149012 A1 | 7/2005 | Penny et al. |
| 2005/0159738 A1 | 7/2005 | Visram et al. |
| 2005/0203504 A1 | 9/2005 | Wham et al. |

(56) References Cited

U.S. PATENT DOCUMENTS

| | | |
|---|---|---|
| 2005/0203507 A1 | 9/2005 | Truckai et al. |
| 2005/0261607 A1 | 11/2005 | Johansen et al. |
| 2005/0288631 A1 | 12/2005 | Lewis et al. |
| 2006/0041253 A1 | 2/2006 | Newton et al. |
| 2006/0074398 A1 | 4/2006 | Whiting et al. |
| 2006/0079769 A1 | 4/2006 | Whiting et al. |
| 2006/0079787 A1 | 4/2006 | Whiting et al. |
| 2006/0079884 A1 | 4/2006 | Manzo et al. |
| 2006/0085054 A1 | 4/2006 | Zikorus et al. |
| 2006/0089638 A1 | 4/2006 | Carmel et al. |
| 2006/0106375 A1 | 5/2006 | Werneth et al. |
| 2006/0135962 A1 | 6/2006 | Kick et al. |
| 2006/0142756 A1 | 6/2006 | Davies et al. |
| 2006/0189972 A1 | 8/2006 | Grossman |
| 2006/0241586 A1 | 10/2006 | Wilk |
| 2006/0247672 A1 | 11/2006 | Vidlund et al. |
| 2006/0264927 A1 | 11/2006 | Ryan |
| 2006/0276710 A1 | 12/2006 | Krishnan |
| 2007/0060879 A1 | 3/2007 | Weitzner et al. |
| 2007/0066975 A1 | 3/2007 | Wong et al. |
| 2007/0118099 A1 | 5/2007 | Trout, III |
| 2007/0123964 A1 | 5/2007 | Davies et al. |
| 2007/0167775 A1 | 7/2007 | Kochavi et al. |
| 2007/0185522 A1 | 8/2007 | Davies et al. |
| 2007/0208256 A1 | 9/2007 | Marilla |
| 2007/0225681 A1 | 9/2007 | House |
| 2007/0270791 A1 | 11/2007 | Wang et al. |
| 2007/0293924 A1 | 12/2007 | Belden et al. |
| 2007/0299461 A1 | 12/2007 | Elliott |
| 2008/0039834 A1 | 2/2008 | MacKay |
| 2008/0039865 A1 | 2/2008 | Shaher et al. |
| 2008/0042360 A1 | 2/2008 | Veikley |
| 2008/0086120 A1* | 4/2008 | Mirza ................ A61B 18/1482 606/41 |
| 2008/0097213 A1 | 4/2008 | Carlson et al. |
| 2008/0108902 A1 | 5/2008 | Nita et al. |
| 2008/0108987 A1 | 5/2008 | Bruszewski et al. |
| 2008/0146918 A1 | 6/2008 | Magnin et al. |
| 2008/0161794 A1 | 7/2008 | Wang et al. |
| 2008/0171934 A1 | 7/2008 | Greenan et al. |
| 2008/0194999 A1 | 8/2008 | Yamaha et al. |
| 2008/0208121 A1 | 8/2008 | Youssef et al. |
| 2008/0275439 A1 | 11/2008 | Francischelli et al. |
| 2009/0105742 A1 | 4/2009 | Kurth et al. |
| 2009/0138009 A1 | 5/2009 | Mswanathan et al. |
| 2009/0163850 A1 | 6/2009 | Betts et al. |
| 2009/0163913 A1* | 6/2009 | Wang ................ A61B 18/1492 606/41 |
| 2009/0177114 A1 | 7/2009 | Chin et al. |
| 2009/0264977 A1 | 10/2009 | Bruszewski et al. |
| 2010/0076404 A1 | 3/2010 | Ring |
| 2010/0087789 A1 | 4/2010 | Leeflang et al. |
| 2010/0125282 A1 | 5/2010 | Machek et al. |
| 2010/0168684 A1 | 7/2010 | Ryan |
| 2010/0179632 A1 | 7/2010 | Bruszewski et al. |
| 2010/0191142 A1 | 7/2010 | Paul et al. |
| 2010/0194047 A1 | 8/2010 | Sauerwine |
| 2010/0204560 A1 | 8/2010 | Salahieh et al. |
| 2011/0046619 A1 | 2/2011 | Ducharme |
| 2011/0118735 A1 | 5/2011 | Abou-Marie et al. |
| 2011/0152716 A1 | 6/2011 | Chudzik et al. |
| 2011/0160592 A1 | 6/2011 | Mitchell |
| 2011/0190763 A1 | 8/2011 | Urban et al. |
| 2012/0029444 A1 | 2/2012 | Anderson et al. |
| 2012/0172857 A1* | 7/2012 | Harrison ............ A61B 18/1477 606/41 |
| 2012/0232546 A1 | 9/2012 | Mirza et al. |
| 2012/0265055 A1 | 10/2012 | Melsheimer et al. |
| 2012/0330156 A1 | 12/2012 | Brown et al. |
| 2013/0184551 A1 | 7/2013 | Paganelli et al. |
| 2013/0184735 A1 | 7/2013 | Fischell et al. |
| 2013/0282084 A1 | 10/2013 | Mathur et al. |
| 2014/0206987 A1 | 7/2014 | Urbanski et al. |
| 2014/0296769 A1 | 10/2014 | Hyde et al. |
| 2016/0220741 A1 | 8/2016 | Garrison et al. |
| 2019/0021763 A1 | 1/2019 | Zhou et al. |
| 2019/0247035 A1 | 8/2019 | Gittard et al. |

FOREIGN PATENT DOCUMENTS

| | | |
|---|---|---|
| JP | H0280058 | 3/1990 |
| JP | H 10-43302 A | 2/1998 |
| JP | 2004216130 | 8/2004 |
| JP | 2007-508113 A | 4/2007 |
| JP | 2008508969 | 3/2008 |
| JP | 2008-194457 A | 8/2008 |
| JP | 2008-529610 A | 8/2008 |
| JP | 2008-245765 | 10/2008 |
| JP | 2008245765 | 10/2008 |
| JP | 2017512569 | 7/2017 |
| WO | 2008/098203 | 8/2008 |
| WO | 2008/098203 A1 | 8/2008 |
| WO | 2009/158060 | 12/2009 |
| WO | 2012/014860 | 2/2012 |
| WO | 2012/044897 A1 | 4/2012 |

OTHER PUBLICATIONS

Japanese Office Action from corresponding JPO application 2021-126775, dated Jun. 29, 2022, Japan Patent Office, 5 pages.

Extended European Search Report from corresponding EPO Application No. 21215791.1, dated Apr. 4, 2022, European Patent Office, 8 pages.

International Search Report and Written Opinion received for PCT Patent Application No. PCT/IB2012/056315, dated Jul. 30, 2013, 12 pages.

Patent Cooperation Treaty, International Preliminary Report on Patentability, International Application No. PCT/IB2012/056315, dated Dec. 2, 2014.

Search Opinion for European Patent Application No. 12877833.9.

* cited by examiner

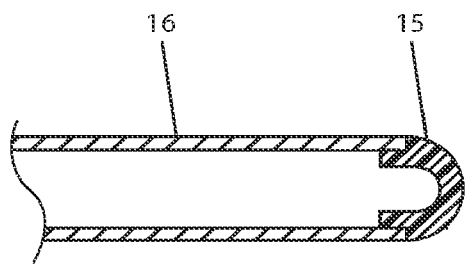 
Fig. 8A  Fig. 8B
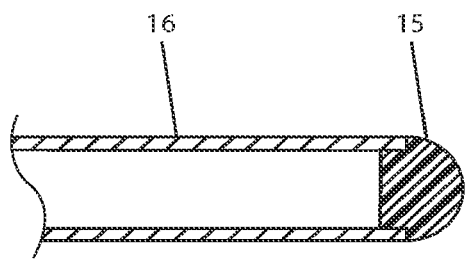 
Fig. 8C  Fig. 8D

RADIOFREQUENCY PERFORATION APPARATUS

TECHNICAL FIELD

The disclosure relates to improving the visualization of medical devices, in particular, devices with lumens for fluid flow.

BRIEF DESCRIPTION OF THE DRAWINGS

In order that the invention may be readily understood, embodiments of the invention are illustrated by way of examples in the accompanying drawings, in which:

FIG. 6a is a diagrammatic side view of a device with a lumen and an internal marker between the ends of the lumen;

FIG. 6b is a diagrammatic end view of the device of FIG. 6a;

FIG. 7a is a diagrammatic side view of a device with a lumen and a hollow internal marker prior to fusion-welding;

FIG. 7b is a diagrammatic end view of the device of FIG. 7a;

FIG. 8a is a diagrammatic side view of the device of FIG. 7a following fusion-welding;

FIG. 8b is a diagrammatic end view of the device of FIG. 8a;

FIG. 8c is a diagrammatic side view of the device of FIG. 7c following fusion-welding;

FIG. 8d is a diagrammatic end view of the device of FIG. 8c;

DETAILED DESCRIPTION

Figure 1:
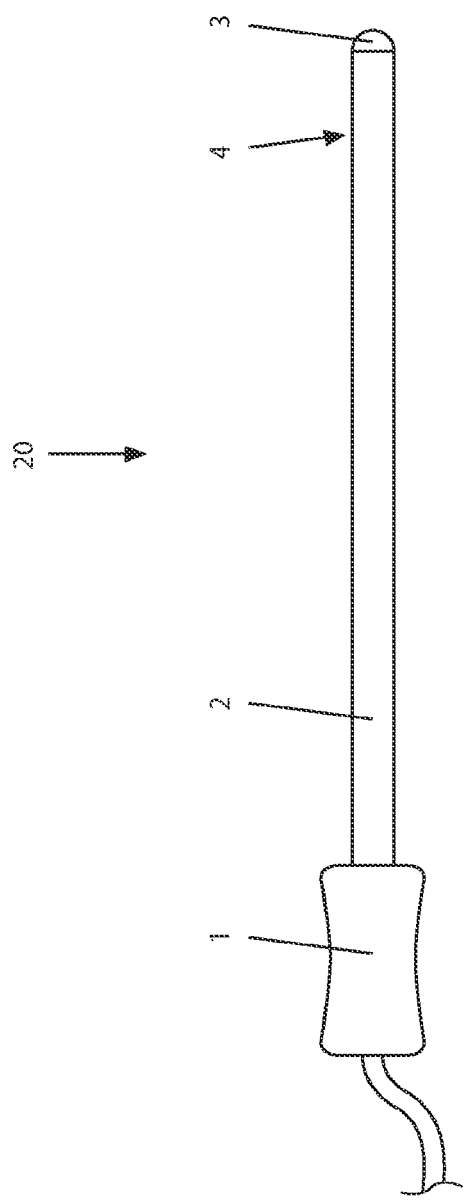
FIG. 1 is an illustration of an embodiment of a device including a handle and shaft.

Certain medical procedures require the use of a medical device that can: create punctures or channels into or through material; enable fluid delivery and/or withdrawal into/from the patient's body; and provide imaging markers for visualizing one or more steps of a medical procedure. Radiopaque bands placed on the outside of a shaft of a medical device are commonly used for imaging. Such external marker bands increase the outer diameter of a device and, in some cases, external dimensional restraints may require reduced outer diameter thereby preventing use of a device with such an external marker. Also, such external marker bands are commonly proximal of the furthermost tip of the device such that the bands do not provide for precise positioning of the tip of a device. To avoid increasing the outer diameter of a device, imaging markers may be placed inside of the device's lumen, but: a) this is often not easily achievable, depending on the size and configuration (material, etc.) of the device and the diameter of the lumen defined by the device; and b) this generally obstructs fluid flow through the lumen of the device.

The present inventors have discovered and reduced to practice several embodiments described herein allowing for improving visualization of a portion of a medical device for inserting into a patient while minimizing obstruction of fluid flow through a lumen and, in addition, avoiding an increase in the outer diameter of the device. This may be accomplished, for example, by providing a radiopaque marker distal to lumen openings (exit ports/apertures) where the diameter of the marker is less than or equal to the diameter of a portion of the device adjacent the marker, or, where the device comprises a metallic tube or similar structure, by providing an imaging marker substantially embedded into/within a wall of the tube.

One specific embodiment includes a hemispherical atraumatic distal tip comprising radiopaque material fusion-welded with the end of a metal tube to form a radiopaque electrode tip at the distal tip of the device. The radiopaque electrode tip provides for both positioning of the distal end of the device and delivering energy, while the atraumatic shape largely limits or prevents accidental damage to tissue. This embodiment may also include longitudinally extended lateral side ports (lateral apertures) for fluid flow. Aspects of the embodiments described herein can also be included in other types of devices, for example, devices without a lumen for fluid flow, and devices not providing energy delivery.

In a first broad aspect, embodiments of the present invention include a medical device comprising an elongated member having a proximal end, a distal end, and a metal tube including an open distal end which is forward facing, the metal tube defining a lumen extending substantially between the proximal end and the distal end of the elongated member, and the elongated member defining a side port from the lumen to an environment outside of the elongated member. An electrode extends distally of the open distal end of the metal tube to define a distal tip of the medical device, with the electrode being configured for delivering electrical energy, wherein the electrical energy is delivered to the electrode through the metal tube. An imaging marker is comprised of an electrically conductive metal associated with the elongated member at a marker location, with the imaging marker being in electrical communication with the metal tube of the elongated member, wherein the medical device is configured such that, in use, a flow of fluid through the lumen to the side port is not substantially obstructed by the imaging marker. The imaging marker is located at the distal end of the metal tube, wherein the imaging marker substantially occludes the lumen at the distal end of the metal tube to prevent the flow of fluid in the lumen flowing past the marker location, and a portion of the imaging marker fills a portion of the lumen between the side port and the distal end of the elongated member and another portion of the imaging marker extends beyond the open distal end of the metal tube to outside of the lumen to define at least part of the electrode.

In typical embodiments of the first broad aspect, the portion of the imaging marker which fills the portion of the lumen has a cylindrical shape and a solid cross-section. Typical embodiments include the electrode being round shaped and atraumatic such that the electrode extends distally of the open distal end of the metal tube to define a distal tip of the medical device being round shaped and atraumatic. Alternative embodiments include the electrode having a pointed shape such that the electrode extends distally of the open distal end of the metal tube to define a distal tip of the medical device having a pointed shape. In typical embodiments, an outer diameter of the medical device at the marker location is substantially equal to the outer diameter of the medical device adjacent to the marker location.

Typical embodiments of the first broad aspect comprise a layer of insulation which covers the metal tube to distal of the side port and leaves a distal portion of the metal tube exposed, and the distal end of the elongated member comprising a functional tip which includes the imaging marker and the electrode, wherein the imaging marker is comprised of electrically conductive metal attached to the distal portion of the metal tube, and the electrode is comprised of the portion of the functional tip which extends beyond the layer of insulation. In some such embodiments, the imaging marker is comprised of metal which is more radiopaque than the metal tube. In some embodiments, the imaging marker is substantially comprised of a radiopaque material.

In some embodiments of the first broad aspect, the medical device further comprises a layer of insulation covering at least some of the elongated member and slightly overlapping a perimeter of the side port to thereby prevent the metal tube from contacting a surrounding tissue while not covering a center of the side port to define an overlap which does not contact the metal tube. In some such embodiments, the side port is longitudinally elongated to provide for increased fluid flow.

In some embodiments of the first broad aspect, the imaging marker is an echogenic marker. In some embodiments, the imaging marker is a marker visible under magnetic resonance imaging. Some embodiments comprise the imaging marker being a radiopaque marker comprising a radiopaque material selected from the group consisting of platinum, iridium, gold, palladium, tungsten, and alloys thereof. In some embodiments having a radiopaque marker, the radiopaque material is comprised of about 90% platinum and about 10% iridium. In some embodiments having a radiopaque marker, the radiopaque material is comprised of about 92% platinum and about 8% tungsten.

Some embodiments of the first broad aspect include a layer of electrical insulation along an outer surface of the metal tube. In some examples, the metal tube is comprised of a proximal metal tube and a distal metal end member in electrical communication with the proximal metal tube. Examples having a proximal metal tube and a distal metal end member typically include a layer of insulation covering at least some of the proximal metal tube and some of the distal metal end member, leaving a distal portion of the distal metal end member exposed to define at least a part of the electrode. In some such examples, the distal metal end member defines the open distal end of the metal tube and where the distal metal end member includes a functional tip which includes the electrode and the imaging marker, wherein the imaging marker is comprised of electrically conductive metal attached to a distal portion of the distal metal end member, and the electrode is comprised of the portion of the functional tip which extends beyond the layer of insulation. Some such examples include the layer of insulation which covers the metal tube extending beyond the metal tube to cover a portion of the functional tip which is proximal of the electrode.

In some embodiments of the first broad aspect, the elongated member comprises a plastic tube and in others the elongated member comprises a metal tube. The elongated member can alternatively be a round tube, a coil, a braid or a conduit that is not round. Embodiments having a metal tube can further comprise the imaging marker being attached to the metal tube by welding, and further that the functional tip is formed by fusion welding of a distal end of the metal tube and a radiopaque filler or other radiopaque material with the functional tip possibly having at least a dome or hemispherical-shaped portion and that the functional tip blocks the distal end of the lumen.

In a second broad aspect, embodiments of the present invention include a method of creating a channel or perforation at a target location in a body of a patient, using a medical device comprising an elongated member and a functional tip associated with the elongated member and located about a distal end of the elongated member, at least a portion of the functional tip being visible using a medical imaging modality, the method comprising the steps of: a) visualizing the functional tip as the medical device is advanced through the patient's body to guide the functional tip to the target location; c) positioning the functional tip at the target location; and d) delivering electrical energy through an electrode of the functional tip to create the channel or perforation.

Some embodiments of the method of creating a channel or perforation at a target location in a body of a patient comprise the steps of: a) introducing a medical device comprising an elongated member, and a functional tip associated with and located at/about a distal end of the elongated member, into the vasculature of the patient, b) advancing the medical device through the vasculature using the functional tip as a radiopaque marker for imaging of the distal end whereby the distal end can be steered, c) positioning the functional tip to the target location, and d) delivering electrical energy through an electrode of the functional tip electrode to create the channel.

In some embodiments of the second broad aspect, the elongated member defines a lumen and the medical device has at least one opening from the lumen to the environment outside of the elongated member and the method further comprises the step of fluid flowing through the opening. In some embodiments, a distal end of the lumen is closed and the elongated member has at least one lateral aperture (side port) from the lumen to the environment outside of the elongated member, and the method further comprises the step of fluid flowing through the sideport. Fluids, such as fluids visible under imaging, can be delivered or withdrawn.

In some embodiments of the second broad aspect, step b) further comprises advancing the elongated member through the vasculature without substantial coring of tissue. In some embodiments, step d) further comprises creating the channel without substantial coring of tissue.

In some embodiments of the second broad aspect, the functional tip has a diameter that is less than or equal to an outer diameter of the elongated member (the shaft of the device) to thereby ease or facilitate the advancement of the elongated member through vasculature i.e. the functional tip does not increase the outer diameter of the device, which would make advancement more difficult.

Optionally, in some embodiments, the energy that is delivered in step d) is radio frequency electrical energy.

In some embodiments of the second aspect of the invention, the elongated member defines a lumen and the medical device has at least one opening from the lumen to an environment outside of the elongated member, and the method further comprises the step of using fluid to sense pressure. In some such embodiments, the fluid comprises a liquid. In alternative embodiments, the fluid comprises a gas. In other alternative, the fluid comprises particles of solid that can flow, possibly echogenic marker beads.

In alternative embodiments of the medical device, an imaging marker can be echogenic, magnetic (i.e. a marker visible using magnetic resonance imaging) or some other type of imaging marker. Consequently, while some of the embodiments of this disclosure are described as having radiopaque markers, said radiopaque markers can have replaced by or supplemented by said echogenic markers, magnetic (i.e. a marker visible using magnetic resonance imaging) markers or other types of markers to result in alternative embodiments. Furthermore, while the end of the functional tip is shown as being dome-shaped in some of the figures, it can be other shapes, including, but not limited to, pointed or knife-like.

With specific reference now to the drawings, it is stressed that the particulars shown are by way of example and for purposes of illustrative discussion of certain embodiments of the present invention only. Before explaining embodiments of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

For the purposes of this description, proximal indicates next to or nearer to the user, and distal indicates further away from the user. In addition, alternative terminology has been used throughout the specification and is generally indicated by the use of regular brackets such as ( ). Furthermore, although several embodiments are described in conjunction with metal, metallic tubes, etc., it should be noted that other materials exhibiting similar material characteristics, such as electrical conductivity, are included as well.

One possible general embodiment of a device 20 is shown in FIG. 1. It comprises a handle 1, a shaft or elongated member 2, and a distal portion 4 of elongated member 2. A functional tip that has an electrode 3 is associated with the distal tip of distal portion 4. Electrode 3 is operable to deliver energy. The embodiment of FIG. 1 has an electrode 3 that is dome-shaped, while alternative embodiments may have an electrode 3 that has a different shape, for example (but not limited to), pointed or knife-like. The internal details of elongated member 2 of FIG. 1 may vary. An example of elongated member 2 of FIG. 1 may include a plastic shaft that contains a wire connected to distal electrode 3, while an alternative example of elongated member 2 of FIG. 1 may include an electrically conductive metal tube covered with electrical insulation. In other alternative embodiments, elongated member 2 may comprise of a coil, braid or a conduit that is not round. The part of the device that is normally inserted into a patient (the usable part of the device) generally includes (but is not limited to) elongated member 2 and the functional tip. The embodiments of the disclosure include a lumen inside elongated member 2 for fluid flow such that fluid can be delivered or removed through the lumen (or conduit), or used for pressure sensing. The fluid may be gas, liquid, or particles of solid that can flow. Echogenic marker beads are an example of particles of solid that may flow. The distal tip electrode is an optional feature of the invention and is not found in some alternative embodiments.

Figure 5:
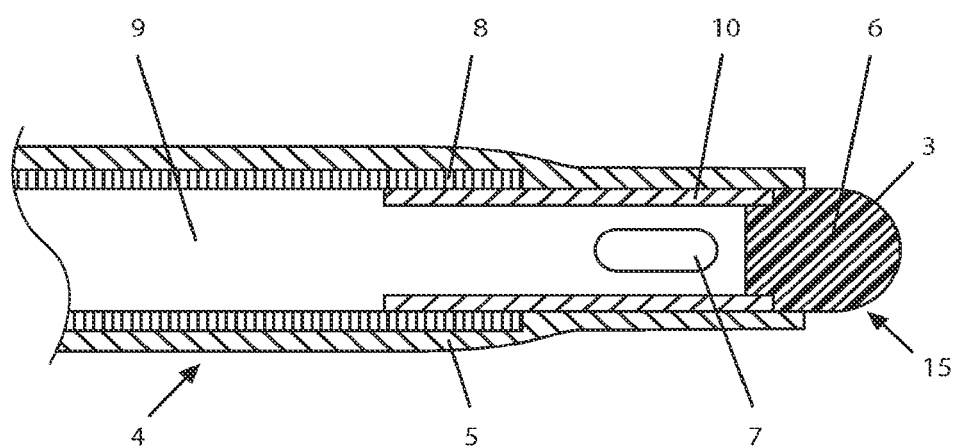
FIG. 5 is a side cutaway view of a distal portion of an embodiment of a device.

Making reference to FIG. 5, a possible embodiment of the invention includes elongated member 2 being comprised of metal tube 8 which is in electrical communication with metal end member 10. Insulating layer 5, which may be PTFE (polytetrafluoroethylene), covers metal tube 8 and some of end member 10, leaving a distal portion of metal end member 10 exposed to define an electrode 3. Metal tube 8 and metal end member 10 can be comprised of, but are not limited to, stainless steel. The distal end of end member 10 includes a functional tip 15 that includes the aforementioned electrode 3 and a radiopaque marker 6. A possible method to produce functional tip 15 includes inserting radiopaque filler (or other radiopaque material) inside the distal end of end member 10 and then fusion welding said distal end to close off lumen 9 at the end of end member 10. The radiopaque filler can possibly comprise platinum, iridium, gold palladium, tungsten, or other radiopaque metal or alloys thereof, such as for example an alloy of about 90% platinum and about 10% iridium, or an alloy of about 92% platinum and about 8% tungsten. The portion of functional tip 15 extending beyond insulating layer 5 functions as electrode 3. The radiopaque part of the fusion welded material forms radiopaque marker 6. Depending on how far distally insulating layer 5 extends along distal portion 4, part, all, or none of radiopaque marker 6 can be covered by the insulating layer. Consequently, electrode 3 can possibly contain part, all, or none of radiopaque marker 6. The configuration of the metals in the fusion weld can vary depending on a number of factors related to the welding process, some (but not all) of the factors including: the amount and type of radiopaque filler used in making the weld, the thickness and type of metal of end member 10, the period of time that energy is applied to the materials, and the energy level.

This embodiment also includes lumen 9 and lateral aperture (side port opening) 7 for movement of fluid between the lumen and the environment outside of the device. Lumen 9 is blocked (or closed) at the distal end of end member 10 by functional tip 15. Opening 7 is closer to the proximal end of elongated member 2 than is functional tip 15, whereby functional tip 15 does not obstruct fluid flowing through opening 7. Electricity may be delivered through metal tube 8 and end member 10 to electrode 3.

Figure 2A:
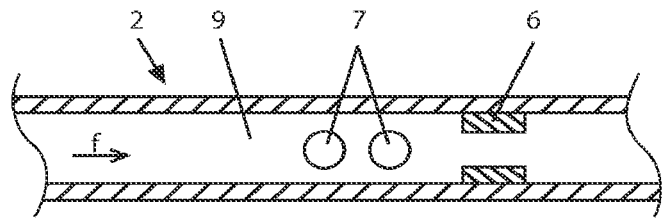
FIGS. 2a-2d are diagrammatic side views illustrating different embodiments having a shaft or elongated member with a lumen, and a marker that is distal of an opening(s)

The embodiment of FIG. 5 is an example of an embodiment of the invention having an imaging marker that is more distal than the opening (exit port) through which fluid may exit or enter the lumen of the device. Other examples of embodiments having this feature can be found in FIGS. 2a to 2d. In FIG. 2a, the direction of a possible fluid flow in lumen 9 is indicated by flow arrow f. An imaging marker 6 is attached (coupled) inside of elongated member 2 distal of openings (side ports) 7. The distal end of lumen 9 (not shown) is closed by any of various possible means. Imaging marker 6 can be different shapes including, but not limited to, a ring-shaped hollow band or a coil. Elongated member 2 may be comprised of plastic, other polymers, metal, or other materials.

Figure 2B:
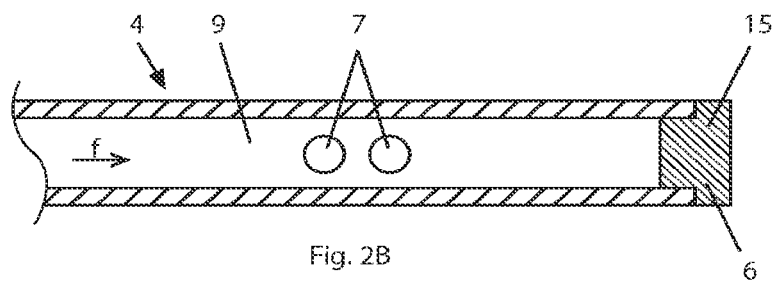

FIG. 2b is a diagrammatic side view showing a functional tip 15 that includes an imaging marker 6, attached (coupled) to the end of distal portion 4 of elongated member 2, thereby blocking or closing lumen 9. The embodiment illustrated in FIG. 2b may have the shaft of distal portion 4 comprised of one or more layers/components of plastic, other polymers, metal, or other materials. Imaging marker 6 can possibly be radiopaque, echogenic, magnetic (i.e. a marker visible using magnetic resonance imaging) or a marker of another type. Marker 6 is distal of openings 7, whereby fluid can exit out of openings 7 without being obstructed by marker 6. Embodiments of FIGS. 2a and 2b having a metal shaft would typically have an insulating layer 5 (not shown) thereupon in a medical device 20.

Figure 2C:
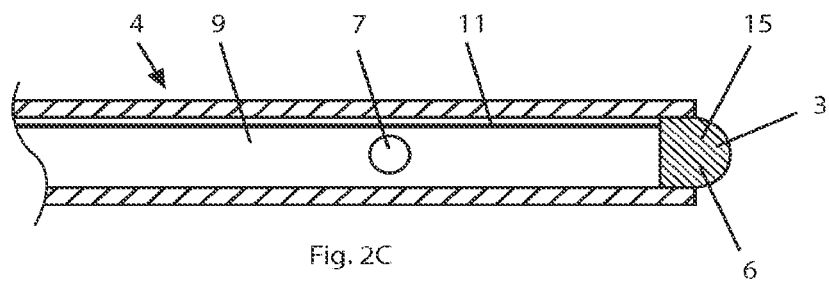

FIG. 2c shows an embodiment with distal portion 4 comprised of a plastic tube. Functional tip 15 closes lumen 9 at the end of distal portion 4. Insulated conducting wire 11 is connected to functional tip 15 whereby energy can be delivered to electrode 3. Functional tip 15 (which includes marker 6) can be attached to the shaft of distal portion 4 using a number of methods, for example, including but not limited to, gluing or engaging mating threads. Lumen 9 can also contain wires for different purposes e.g. fiber optic wires or wires used for pressure sensing.

Figure 2D:
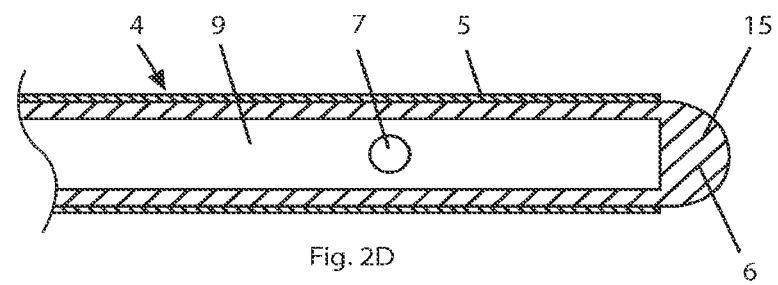

FIG. 2d illustrates an embodiment having distal portion 4 comprising a metal tube and insulating layer 5. Lumen 9 is closed off by a fusion welded functional tip 15 that comprises an end marker 6. Marker 6 is distal of lateral aperture (side port opening) 7. The fusion weld of this embodiment has an alternative weld shape to that of the embodiment of FIG. 5.

Several views of an additional embodiment similar to that of FIG. 2d are shown in FIGS. 10a-10d. The views illustrate electrode 3 and marker 6 of a functional tip 15, aperture 7, lumen 9, and insulating layer 5.

Figure 11A:
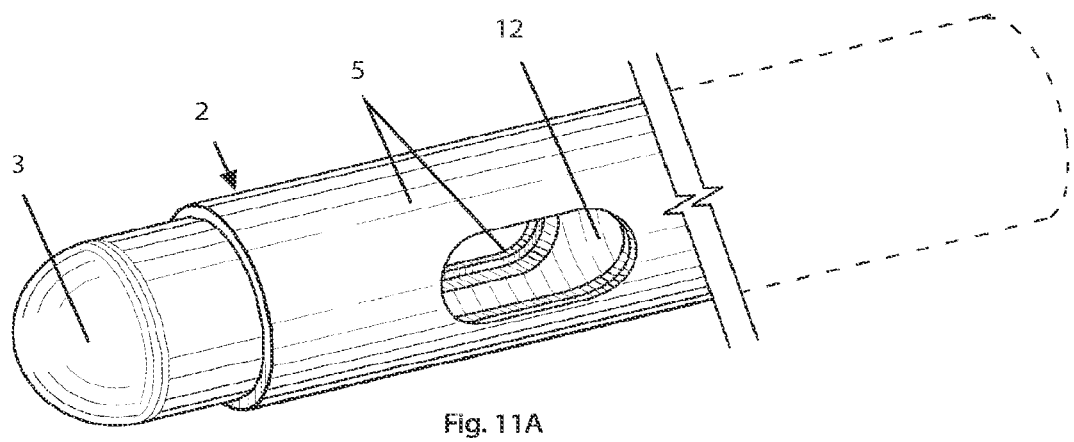
FIGS. 11a-11g show various views of an alternative embodiment of a device of the present invention.
Figure 11B:
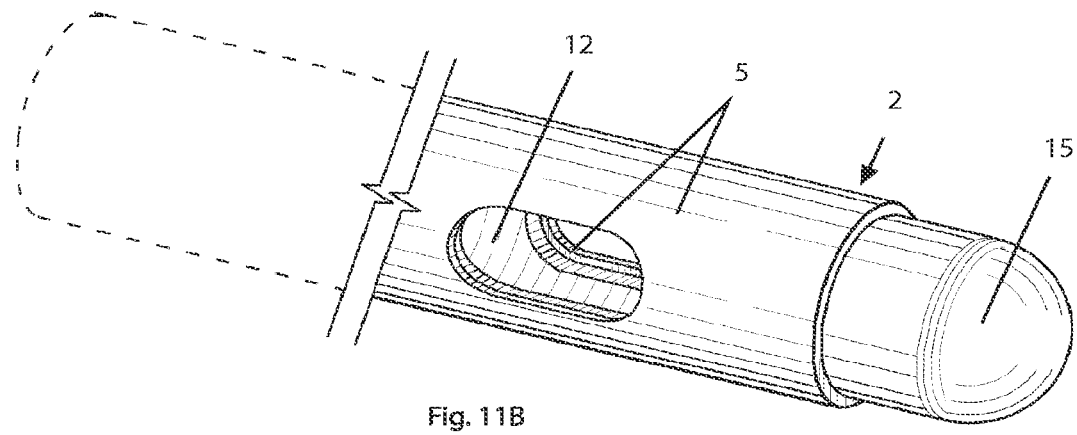
Figure 11C:
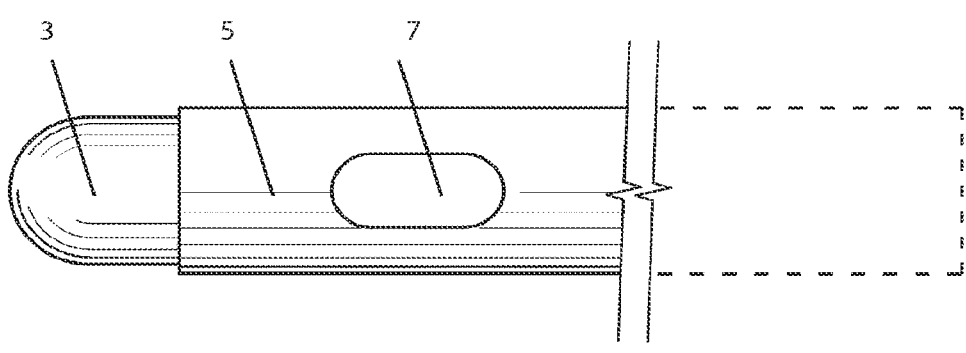
Figure 11D:
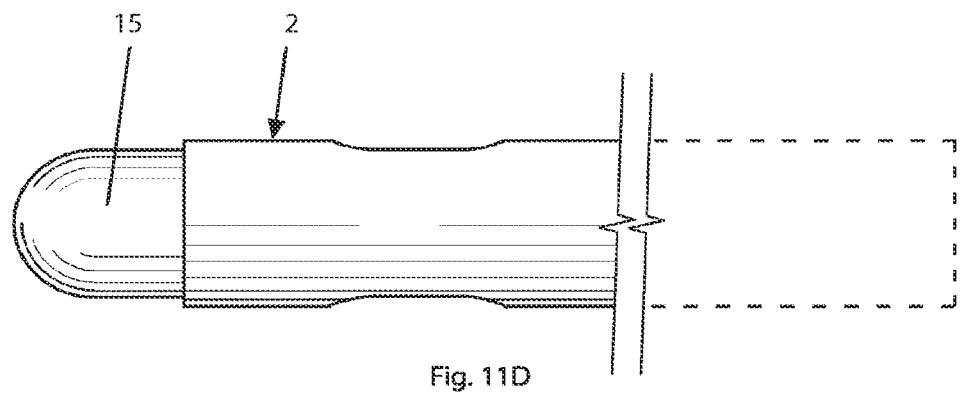
Figure 11E:
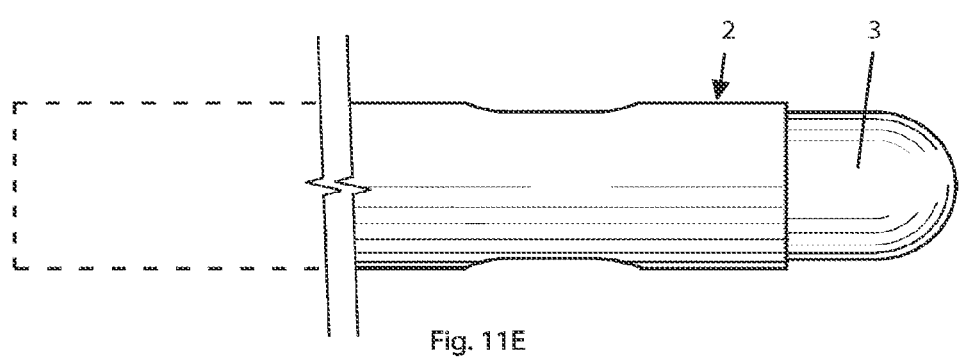
Figure 11F:
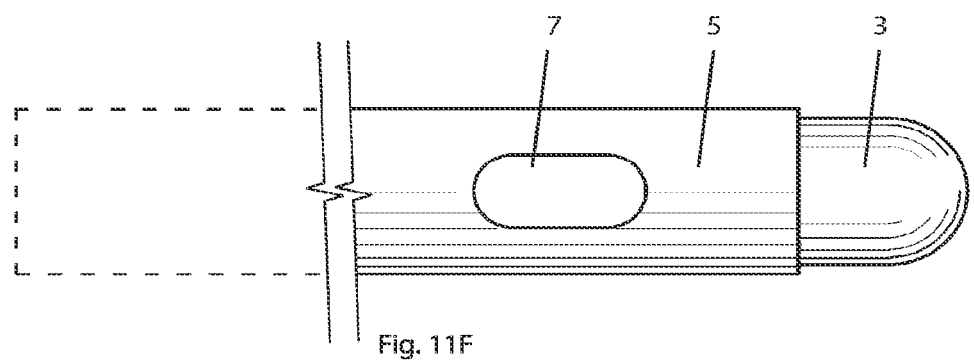
Figure 11G:
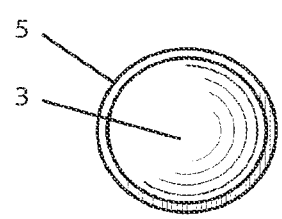

Another embodiment similar to that of FIG. 2d is illustrated in FIGS. 11a-11g, which includes elongated member 2, electrode 3, insulating layer 5, aperture 7, metal tube 12, and functional tip 15. The break lines and the broken lines are included in these figures to indicate the device has an indeterminate length. FIGS. 11a and 11b illustrate that in this embodiment insulating layer 5 slightly overlaps metal tube 12 around lateral aperture 7 (side port 7). Having insulating layer 5 overlap metal tube 12 avoids exposure of metal at aperture 7 and thereby prevents the electrically conductive metal from contacting surrounding tissue. The overlap also reduces current leakage through aperture 7. FIG. 7 illustrates the lateral aperture 7 being longitudinally elongated to provide for increased fluid flow in comparison to a round aperture having a diameter similar to the height (i.e. short dimension) of elongated lateral aperture 7.

Figure 3A:
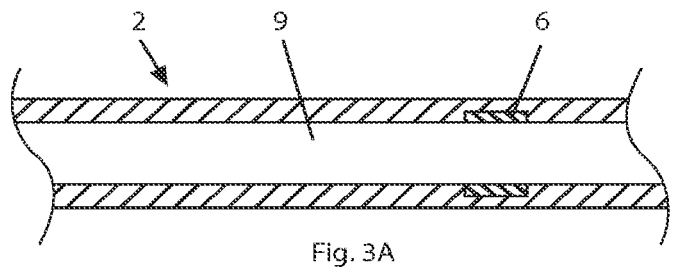
FIGS. 3a-3j are diagrammatic side views illustrating different embodiments having a marker embedded in the wall of a metal tube.
Figure 3B:
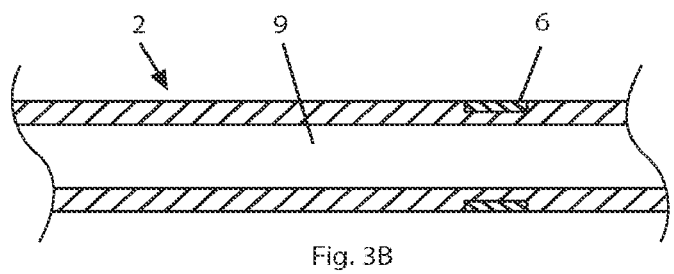

The embodiments found in FIGS. 3a to 3i are examples of embodiments of the invention in which an imaging marking is embedded into a wall of an elongated member. FIG. 3a is an example of an embodiment in which a marker 6 is embedded in the inside surface of the wall of elongated member 2 whereby fluid can flow through lumen 9 without being obstructed and the outer diameter of elongated member 2 is not increased. Marker 6 can be embedded in the inside wall using different techniques, such as overmoulding. FIG. 3b is an example of an embodiment in which a marker 6 is embedded in the outside wall of elongated member 2 whereby fluid can flow through lumen 9 without being obstructed and the outer diameter of elongated member 2 is not increased. Imaging marker 6 can be different shapes including, but not limited to, a ring-shaped hollow band or a coil. Alternative embodiments include imaging markers that are disc-shaped, rectangular, and elongate, that define other geometric shapes, or that define symbols.

For the embodiments of FIGS. 3a and 3b, elongated member 2 can be comprised of one or more layers/components of plastic, other polymers, metal, or other materials. The marker is embedded in a wall which can be either all metal or substantially (mostly) metal. For example, for the marker receiving wall can be covered with a relatively thin layer of polymer, such as the receiving wall of FIG. 3b being covered with a layer of electrical insulation. As all metals are radiopaque to some degree, a radiopaque marker should be more radiopaque than the metal tube to function properly. In general, for any embodiment of the device having a radiopaque marker, the radiopaque marker may be comprised of a material that is more radiopaque than whatever material of elongated member 2 is comprised of. In FIGS. 3a and 3b, the distal end of lumen 9 is open. Embodiments of FIGS. 3a and 3b having a metal shaft can optionally have an insulating layer 5 (not shown).

Figure 3C:
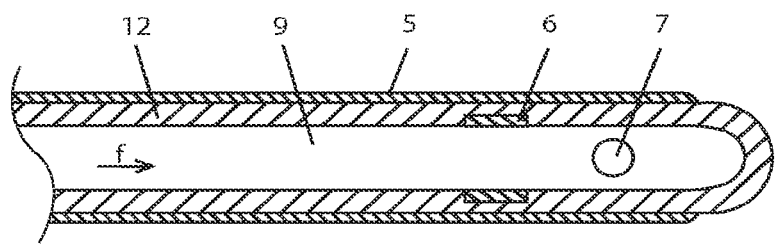
Figure 3D:
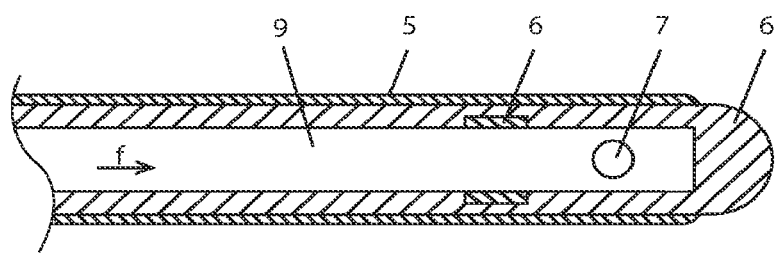
Figure 3E:
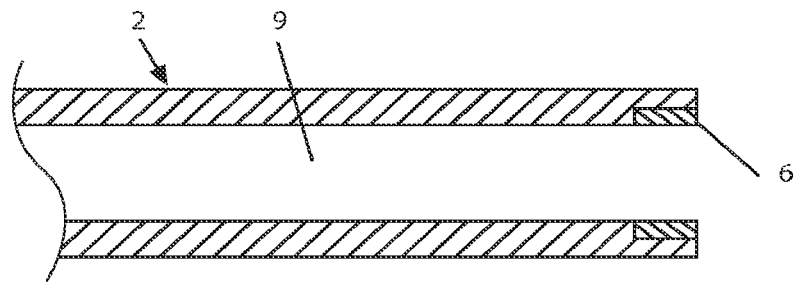
Figure 3F:
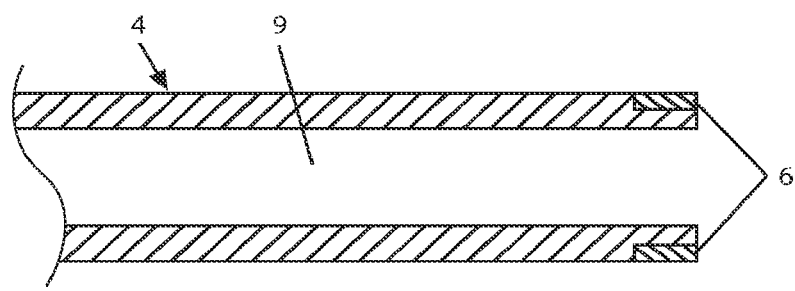
Figure 3G:
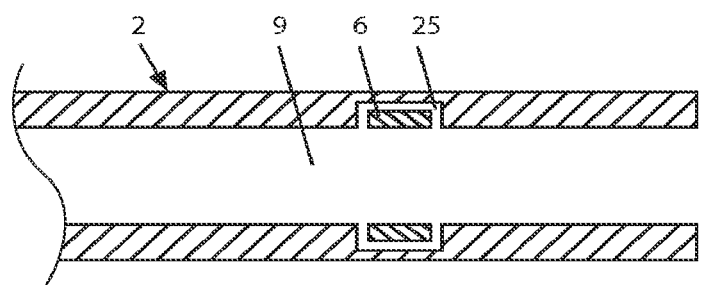
Figure 3H:
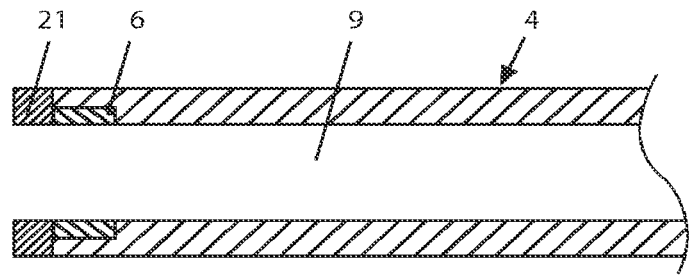
Figure 3I:
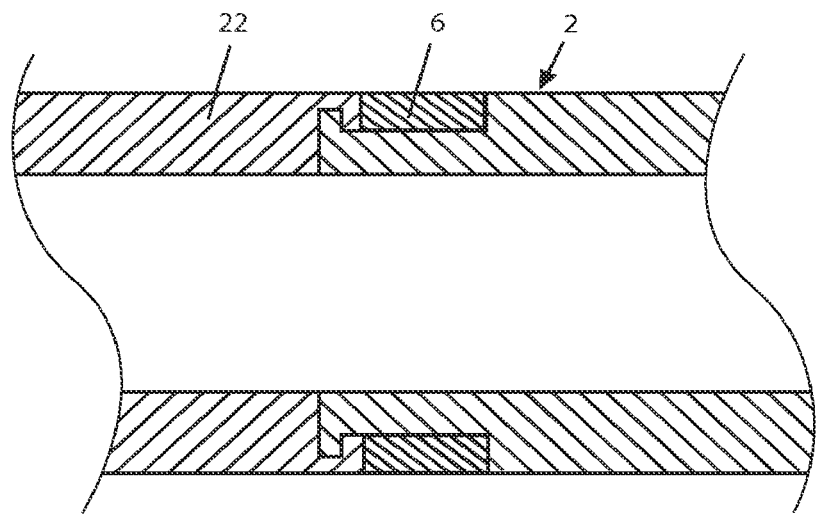
Figure 3J:
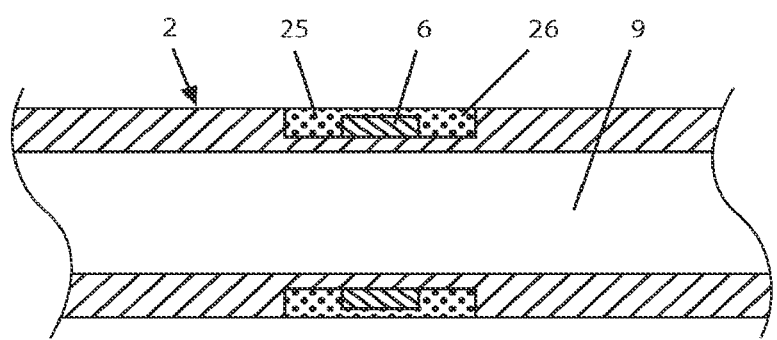

FIG. 3j is an example of an embodiment which is similar to FIG. 3b in that it also includes a marker 6 that is embedded in the outside wall of elongated member 2 whereby fluid can flow through lumen 9 without being obstructed. In the case of the embodiment of FIG. 3j, marker 6 is inside of groove (or channel) 25. As channel 25 has more space than is needed for marker 6, filler 26 is used to occupy the extra space and to possibly provide a constant outer diameter. Groove (or channel) 25 is cut into elongated member 2 such that when marker 6 is seated therein, filler 26 can smooth out the profile of the outer diameter. The filler 26 may be a polymer that is suitable for filling in spaces or gaps.

One method of making the embodiment of FIG. 3j, wherein elongated member 2 is a substrate tubing, comprises: 1) Selectively reducing the outer surface the wall of the substrate tubing (e.g. HDPE—High-density polyethylene) using a process such as centerless grinding to thereby define a groove (or channel) 25; 2) loading the substrate tubing onto a metal mandrel to maintain the lumen and to provide support; 3) swaging a thin walled Pt (platinum) band marker 6 onto the substrate tubing and into channel 25; 4) installing filler 26 material (e.g. Tecoflex®) by reflowing it into the remaining space of groove (or channel) 25 (optionally using a heatshrink to install filler 26); and 5) removing the assembly from the mandrel and removing heatshrink, if it has been used. The heatshrink may aid in providing that device outer dimension at the maker location is the same as the device outer dimension adjacent the marker.

Alternatively, other materials could be used in the embodiment of FIG. 3j. For example, elongated member 2 could be comprised of a metal and band marker 6 comprised of a radiopaque polymer material that can be stretched and installed in groove (or channel) 25.

FIGS. 3c and 3d show embodiments in which a marker 6 is embedded in a metal tube 12 having a closed end. The elongated member also comprises insulating layer 5. FIG. 3c shows a metal tube 12 comprising a tube sidewall and distal end enclosure that are continuous (i.e. that are not separate components) and that have a substantially constant thickness, for example, a hypotube. FIG. 3d illustrates a metal tube 12 closed by a fusion weld. For both of FIGS. 3c and 3d, embedded internal marker 6 does not obstruct fluid flow through opening (side port) 7. The embodiment of FIG. 3d has both an internal lumen marker 6 and an end marker 6.

FIGS. 3e and 3f show embodiments that are similar to the corresponding embodiments of FIGS. 3a and 3b, with difference being that the FIGS. 3e and 3f embodiments have embedded marker 6 located at the distal end of shaft or elongated member 2.

FIG. 3g comprises an internal marker 6 that is not fixedly attached to the surface of the wall defining lumen 9, but instead is capable of limited movement relative to the wall. Marker 6 is contained, in part at least, by a groove (or channel) 25 in the inner surface of the wall of elongated member 2. Marker 6 can be moved a limited distance within groove 25 by a fluid passing through lumen 9. For this embodiment, marker 6 can be referred to as a captive element marker as it is restrained by groove 25 from being carried away by a flowing fluid. Similar to previous embodiments, elongated member 2 can comprise different layers and components, for example, comprising metal covered by insulation.

FIG. 3h discloses an embodiment similar to that of FIG. 3e with the addition of end piece 21. End piece 21 can retain marker 6 in place and/or marker 6 can be held in place by alternative means such as, for example, welding or adhesion. End piece 21 can also have additional/alternative functions such as, for example, providing a smooth end surface.

FIG. 3i discloses an embodiment with the addition of elongated member second component 22. Second component 22 may interlock with a first component of elongated member 2 and retain marker 6 in place and/or marker 6 may be held in place by alternative means such as, for example, welding or adhesion. In some embodiments, second component 22 may be an extension to a relatively larger first part of elongated member 2. In other embodiments second component 22 may be a second part of an elongated member 2 that has a first component or part that is similar in size to (or possibly smaller than) second component 22.

Alternative embodiments of FIGS. 3a to 3i can comprise other types of imaging markers, for example echogenic or magnetic (i.e. a marker visible using magnetic resonance imaging), in addition to or instead of radiopaque markers, for use with the appropriate type of imaging systems and modalities.

Figure 4A:
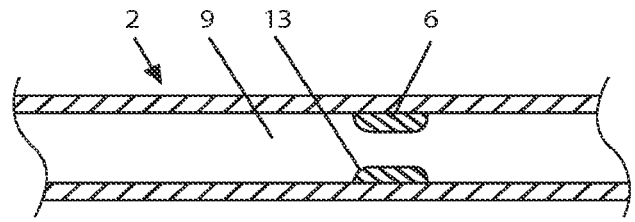
FIGS. 4a-4e are diagrammatic side views illustrating different embodiments having a marker coupled to the inside surface of the wall of a metal tube.

The embodiments found in FIGS. 4a to 4e are examples of embodiments of the invention in which an imaging marker is attached (coupled) to the inner surface of a wall (which can be a metallic tube) of the elongated member, while minimally affecting or obstructing fluid flow within lumen 9. Elongated member 2, including distal portion 4, can be comprised of one or more layers/components of plastic, other polymers, metal, or other materials. Embodiments having a metal shaft may have an insulating layer 5. FIG. 4a is an example of an embodiment in which a ring-shaped band marker 6 is coupled to the inside wall of elongated member 2 whereby fluid can flow through lumen 9 and the outer diameter of elongated member is not increased. The lumen diameter is decreased for only the relatively short length of the lumen containing band marker 6. Rounded edges 13 of the marker can reduce flow turbulence to thereby minimize obstruction of fluid flow. In alternative embodiments, marker 6 can be a coil. The distal end of lumen 9 is open for the embodiments of FIGS. 4a and 4b. For illustrative purposes, the marker is shown as being thicker (relative to elongated member) in the figures than is needed in actual embodiments.

The embodiment of FIG. 4a can be contrasted with adding a marker to the outer surface of a shaft. To maintain the same outer device diameter at the marker's attachment location when a marker is added the outer surface of a shaft, it is necessary to reduce the outer diameter size of the shaft to compensate for the thickness of the marker, which results in a reduced lumen diameter that will impede fluid flow. A hypothetical example can illustrate this point. If a hypothetical shaft has an outer diameter of 10 units and a wall thickness of 1 unit, it would have a lumen diameter of 8 units. If a marker band of 1 unit thickness is attached externally (without bending or crimping of the shaft), maintaining the same total outer diameter of 10 units (for allowing the device to be advanced through particular passages such as body vessels) requires reducing the shaft outer diameter to 8 units and the lumen diameter to 6 units for the length of the shaft (utilizing common manufacturing practices), which would significantly reduce the amount of fluid that can flow through the lumen at a given pressure. Advantageously, installing a marker band of 1 unit thickness within the lumen of the shaft as per embodiments such as described hereinabove, results in a reduction of the lumen diameter to 6 units but only for the length of the marker band (i.e., a relatively short distance), which has a far lesser effect on the volume of fluid flow at a given pressure relative to decreasing the lumen diameter for the entire length of the shaft.

Figure 4B:
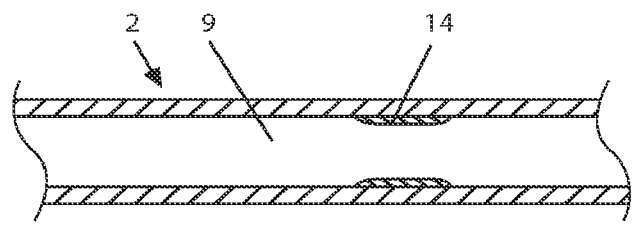

FIG. 4b is an example of an embodiment in which the marker is comprised of a material deposited on the inner wall surface of elongated member 2 by a method such as spray deposition to form deposited layer marker 14. Similar to the embodiment of FIG. 4a, deposited layer marker 14 allows fluid to flow through lumen 9 without significant obstruction while not increasing the outer diameter of elongated member 2. Other methods of depositing a material inside of a lumen include electroplating and sputter deposition (a physical vapor deposition method) of radiopaque material on an interior surface (that defines a lumen) to produce internal band markers or surfaces.

Figure 4C:
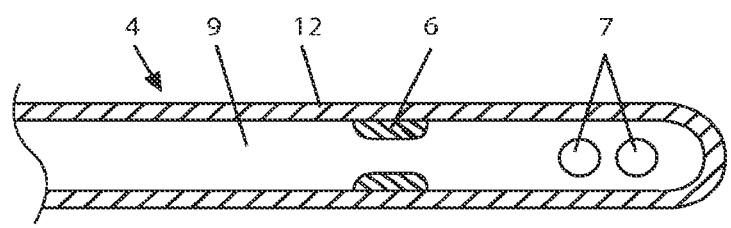

The embodiment of FIG. 4c shows a marker 6 coupled to the inside wall of metal tube 12 that has a closed end. Fluid can flow through lumen 9 and out openings (exit ports) 7 without significant obstruction from the marker and the outer diameter of the elongated member 2 is not increased.

Figure 4D:
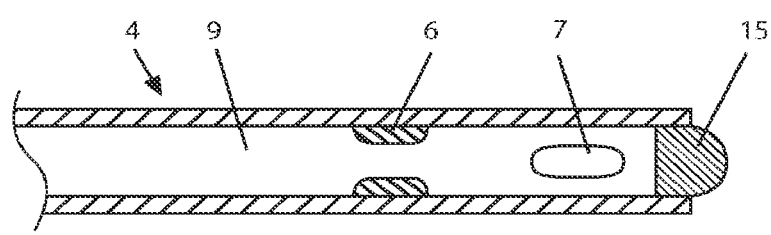

FIG. 4d shows a marker 6 attached to the inner wall of distal portion 4 and a functional tip 15 that closes (or blocks) lumen 9 at the end of distal portion 4. Fluid can flow through lumen 9 and out of openings 7 without significant obstruction and the outer diameter of elongated member 2 is not increased. Functional tip 15 of the embodiment of FIG. 4d may or may not include a marker. Any of the embodiments of FIGS. 4a to 4e can be modified to have the markers 6 or 14 partially embedded into the wall of the device while leaving some of the marker not embedded.

Figure 4E:
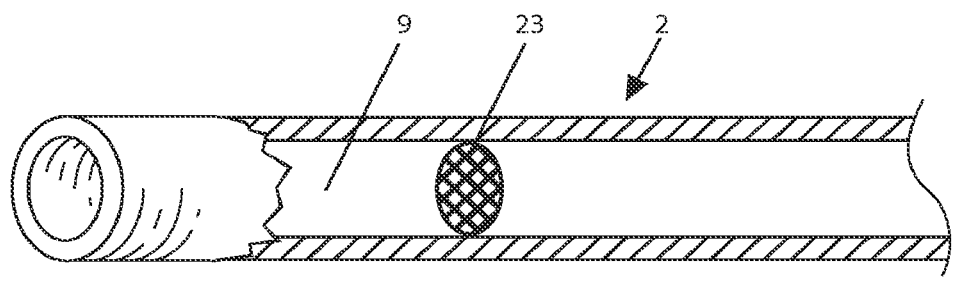

FIG. 4e discloses an embodiment with a marker 6 comprising a plurality of crossing elements located within the lumen of the device. While the embodiment of FIG. 4e illustrates marker 6 as being a grate, in alternative embodiments, marker 6 can comprise a screen, a cross-shaped marker (i.e. two intercepting linear elements), an asterisk-shaped marker, or other configurations having a plurality of crossing elements. The crossing elements allow for the flow of fluid through the lumen while being visible under imaging as distinct from the rest of medical device 20. For this embodiment, marker 6 can either be attached to or at least partially embedded in the surface of the inner wall of elongated member 2.

Figure 4F:
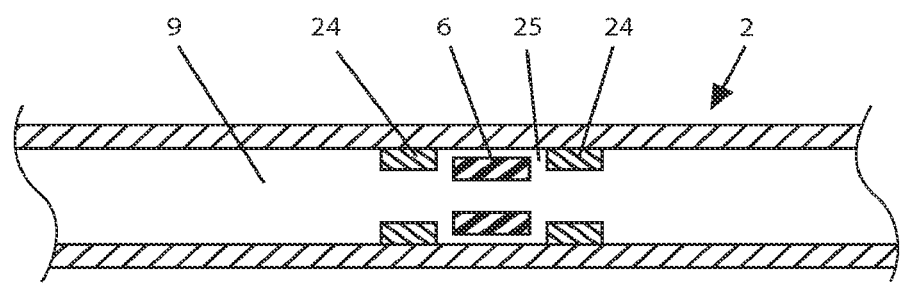
FIG. 4f is a diagrammatic side view illustrating a device with a captive element marker retained by internal retainers coupled to the inside surface of the wall of a metal tube.

FIG. 4f shows a device comprising an internal marker 6 that is not fixedly attached to the surface of the wall defining lumen 9, but instead is capable of limited movement relative to the wall. Marker 6 is restrained by a pair of internal retainers 24 attached the inner surface of the wall of elongated member 2. Marker 6 can be moved a limited distance between the internal retainers 24 by a fluid passing through lumen 9. While internal retainers 24 are shown in FIG. 4f as being separate parts that are attached to the surface of the wall, in alternative embodiments internal retainers 24 can be formed integrally with the wall and project therefrom.

Figures 6A, 6B:
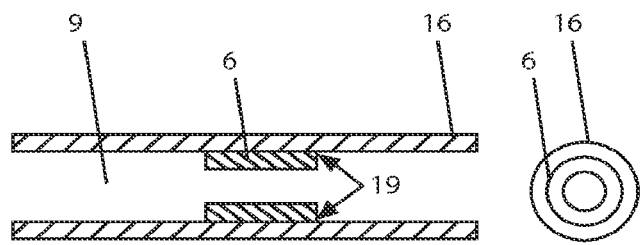

FIGS. 6a and 6b illustrate the positioning of a marker 6 within a lumen 9 and joint(s) 19 that fixes marker 6 into place within the lumen of tubular component 16. Various means can be used to fix marker 6 into place, including:

welding by heating the external surface of tubular component 16,
glue or epoxy,
mechanical deformation (crimping) of the external surface over of tubular component 16, or near the band,
internal welding (with a very small welder, or fiber-optic laser weld system),
interference fit (forcing an oversized ring-shaped band marker 6 into place),
shrinkage fit (by expanding the external tube (tubular component 16) by heat, and shrinking the internal band marker 6 by cooling, sliding the band marker into place, and allowing the external tube to cool while the internal band marker warms up),
external/internal magnets with compatible materials, and
by threading the inner diameter of a tube and the outer diameter of an internal component (parallel with the tube axis) and then engaging.

Figures 7A, 7B:
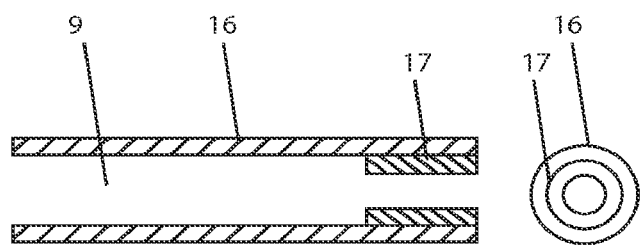
Figures 7C, 7D:
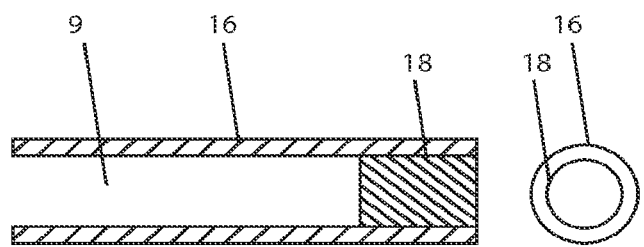
FIG. 7c is a diagrammatic side view of a device with a lumen and a solid internal marker prior to fusion-welding.
FIG. 7d is a diagrammatic end view of the device of FIG. 7c.

FIGS. 7 and 8 illustrate a fusion-welding process for making the end markers of some embodiments. FIG. 7 shows the basic components prior to welding. FIGS. 7a and 7b show side and end views of an embodiment using a hollow marker 17 as filler at the end of the lumen of a tubular component 16. FIGS. 7c and 7d show side and end views of another embodiment using a solid marker 18 as filler at the end of the lumen of another tubular component 16. The material of the filler should be more radiopaque than the material of an associated tubular component 16 if it is to be used to form a radiopaque marker. FIG. 8 shows the devices following welding, with FIGS. 8a and 8b showing side and end views of a functional tip 15 having a fusion weld formed from hollow marker 17 and the end of tubular component 16 of FIG. 7a. FIGS. 8c and 8d show side and end views of a functional tip 15 having a fusion weld formed from solid marker 18 and the end of the tubular component 16 of FIG. 7c. A laser may be used to provide the energy to create the dome shaped functional tip 15. The configuration of the final fusion weld can vary depending on a number of welding factors, some of the factors including: the amount and type of radiopaque filler, the thickness and type of metal of tubular component 16, welding time, and energy intensity.

The configuration of the basic components as illustrated in FIGS. 6 to 8 should not be taken as limiting the embodiments of the invention as other configurations are possible. For example, it is possible that an embodiment can have a pointed tip that is either sharpened or dulled, or a knife-shaped tip or that an embodiment can have an internal hollow marker located at the distal end of a lumen, or that the end is not welded shut.

Some possible options for the above described fusion welding process include tubular component 16 being made with different materials (plastics, metals, etc.), as can the filler. Before welding, the filler can have different shapes and does not have to closely fit the inner diameter of tubular component 16. The filler can comprise a single piece or part, or a plurality of pieces or parts, including particles as small as powder.

The medical device of the disclosure may be used with a source of radiofrequency (RF) energy for creating a channel at a target location in a body of a patient. One such embodiment comprises the steps of: a) introducing a medical device 20 having an elongated member 2 and a distal end functional tip 15 into the vasculature of a patient, b) advancing elongated member 2 through the vasculature using radiopaque marker 6 of functional tip 15 for imaging whereby functional tip 15 (which has an electrode 3) can be steered, c) positioning electrode 3 of functional tip 15 (which is operable to deliver energy) at the target location, and d) delivering electrical energy through electrode 3 to create the channel.

An opening (aperture) 7 can be used to deliver fluid from a lumen 9 of elongated member 2 to the target location. In some embodiments, having the distal end of lumen 9 closed by functional tip 15 and having an opening 7 that is a side port (such as in FIG. 5) helps to prevent coring of tissue. This embodiment includes functional tip 15 having a diameter that is less than the outer diameter of the elongated member to ease or facilitate the advancement of the elongated member through vasculature i.e. the functional tip does not increase the outer diameter of the device which would make advancement more difficult. Optionally, the energy that is delivered to the target location can be radio frequency electrical energy. In alternative embodiments, functional tip 15 may have a portion of it visible under alternative medical imaging modalities, for example, ultrasound or magnetic resonance.

Figure 9A:
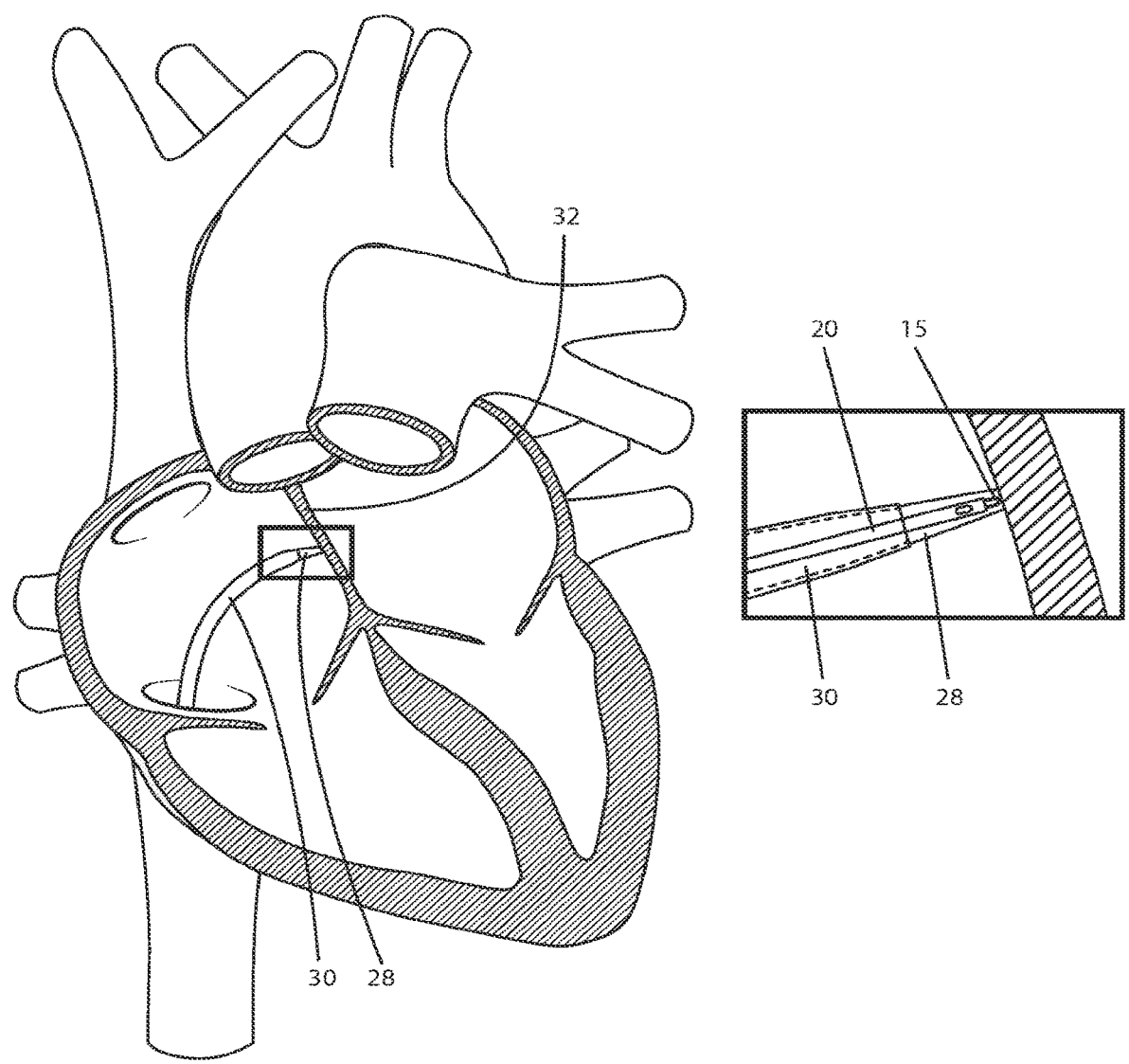
FIGS. 9a and 9b are illustrations of an embodiment of a method of the present invention.
Figure 9B:
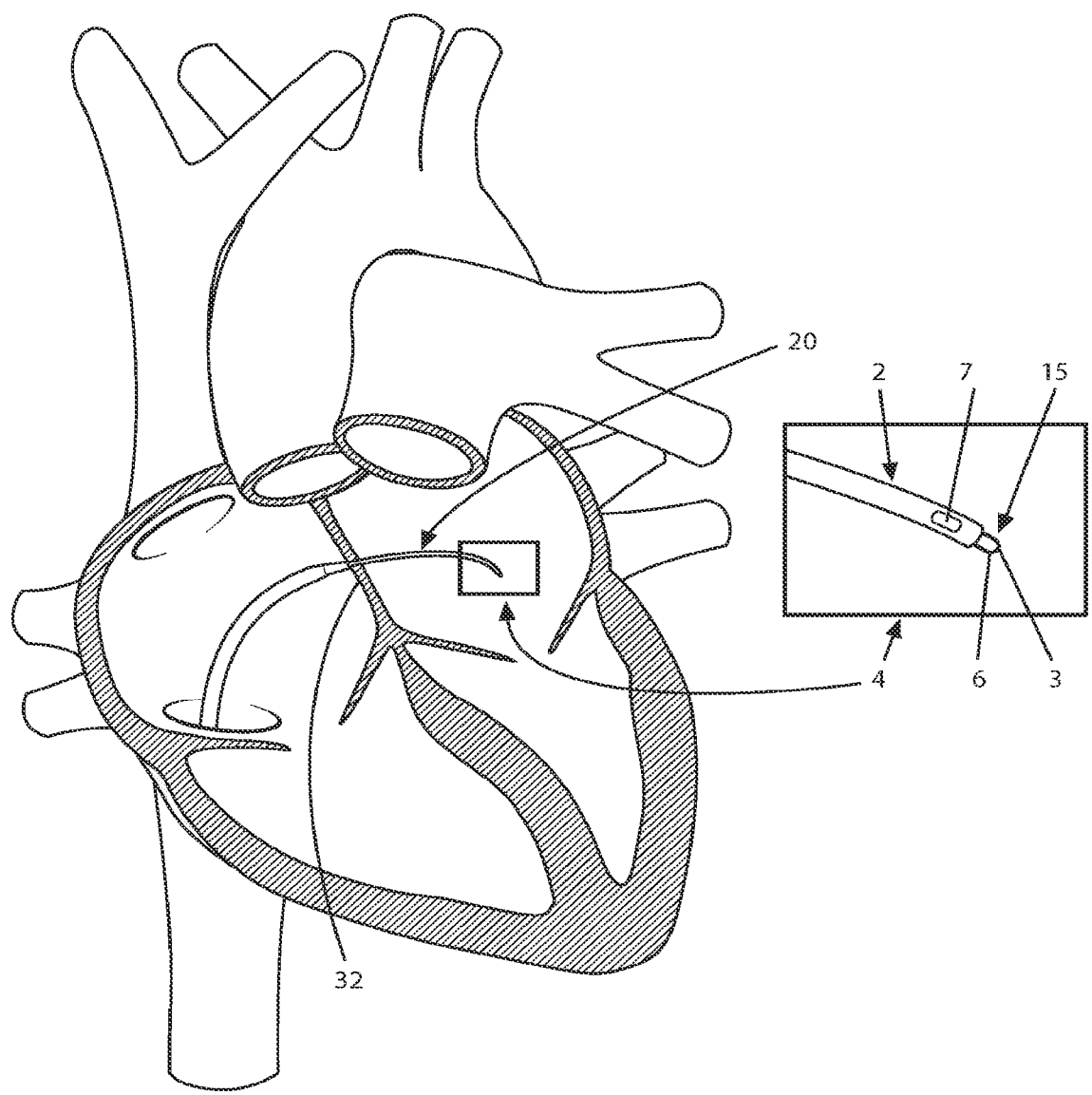
Figure 10A:
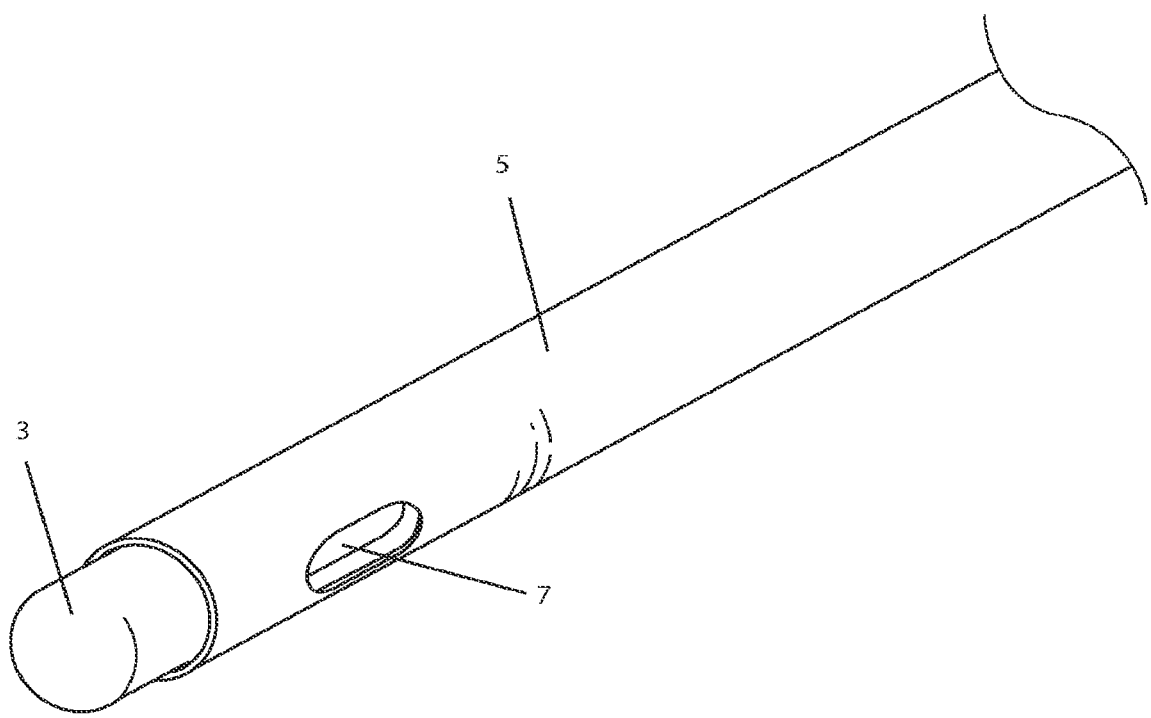
FIGS. 10a-10d show various views of an alternate embodiment of a device of the present invention.
Figure 10B:
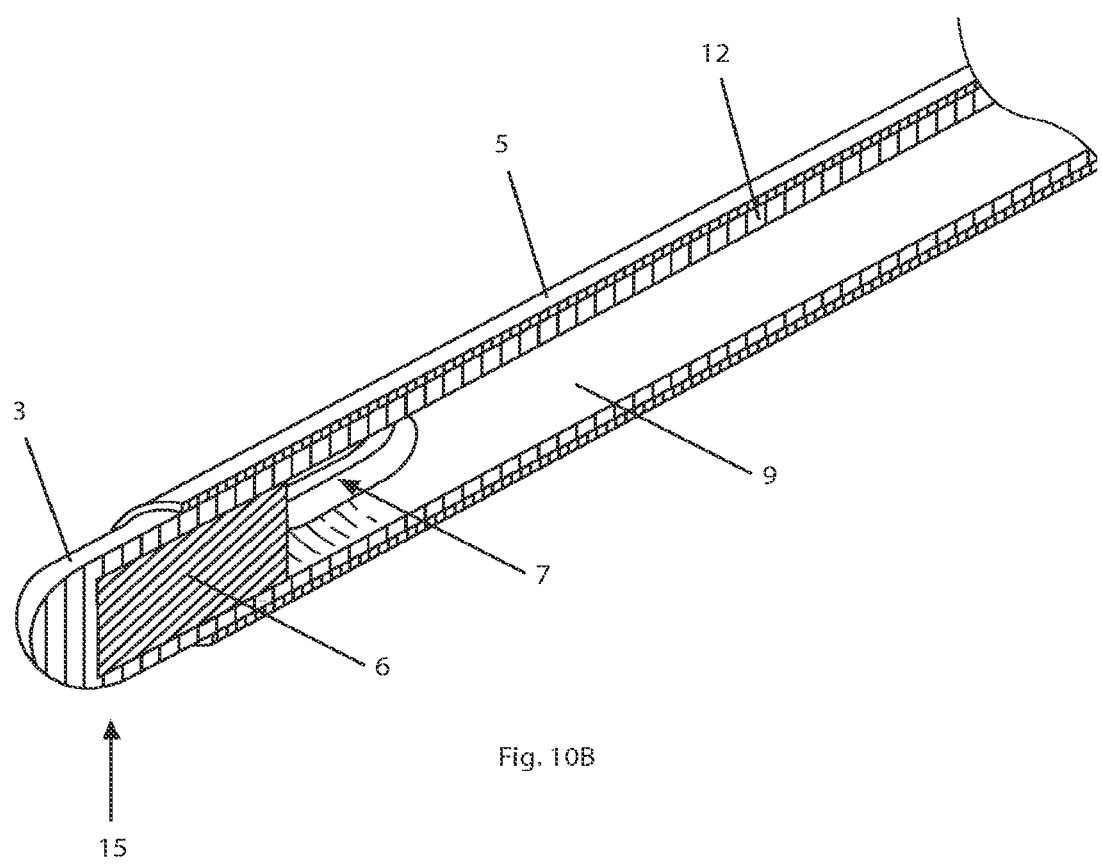
Figure 10C:
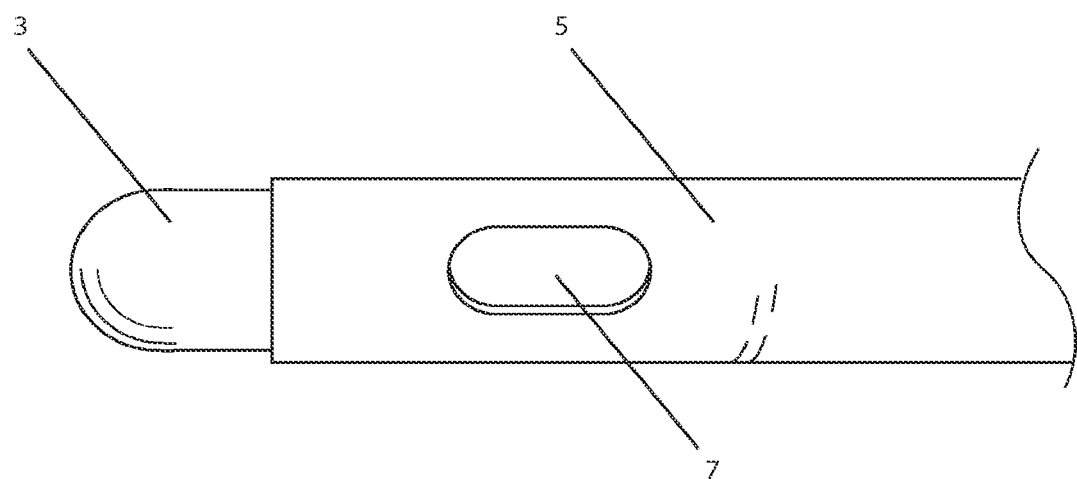
Figure 10D:
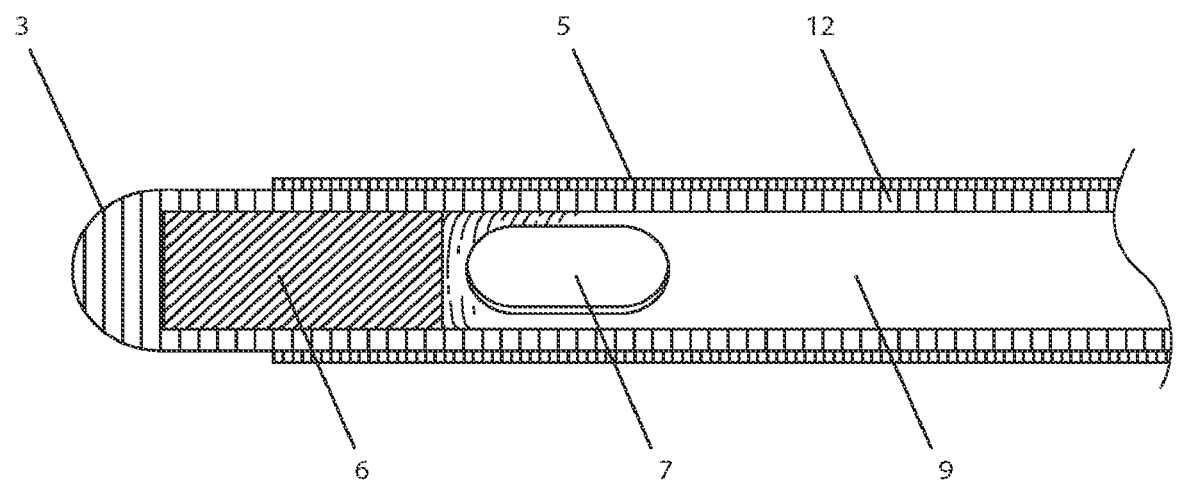

In one specific embodiment of a method of using the disclosed medical device, for example as illustrated in FIGS. 9A and 9B, the target site may comprise a tissue within the heart of a patient, for example the atrial septum of the heart. In such an embodiment, the target site may be accessed via the inferior vena cava (IVC), for example through the femoral vein, with said access being facilitated by imaging of marker 6 of functional tip 15 during advancement of medical device 20 (or radiofrequency perforation apparatus 20). This embodiment includes providing a medical device 20 comprising a functional tip 15 that is visible under imaging so as to be visibly distinct from the rest of the medical device.

In one such embodiment, an intended user introduces a guidewire into a femoral vein, typically the right femoral vein, and advances it towards the heart. A guiding sheath 30, for example a sheath as described in U.S. patent application Ser. No. 10/666,288 (filed on Sep. 10, 2003), incorporated herein by reference in its entirety, is then introduced into the femoral vein over the guidewire, and advanced towards the heart. The distal ends of the guidewire and sheath 30 are then positioned in the superior vena cava. These steps may be performed with the aid of an imaging system appropriate for marker 6. When the sheath 30 is in position, a dilator 28, for example the TorFlex™ Transseptal Dilator of Baylis Medical Company Inc. (Montreal, Canada), or the dilator as described in U.S. patent application Ser. No. 11/727,382 (filed on Mar. 26, 2007), incorporated herein by reference in its entirety, is introduced into the sheath 30 and over the guidewire, and advanced through the sheath into the superior vena cava. The sheath 30 may aid in preventing the dilator 28 from damaging or puncturing vessel walls, for example, in embodiments comprising a substantially stiff dilator. Alternatively, the dilator 28 may be fully inserted into the sheath 30 prior to entering the body, and both may be advanced simultaneously towards the heart. When the guidewire, sheath 30, and dilator 28 have been positioned in the superior vena cava, the guidewire is removed from the body, and the sheath and dilator are retracted slightly, such that they enter the right atrium of the heart. An electrosurgical device, for example radiofrequency perforation apparatus 20 described hereinabove, is then introduced into the lumen of the dilator, and advanced toward the heart.

In this embodiment, after inserting the electrosurgical device into a dilator 28, the user may position the distal end of the dilator against the atrial septum 32. The electrosurgical device is then positioned using imaging of a marker 6 of functional tip 15 such that electrode 3 is aligned with or protruding slightly from the distal end of the dilator 28 but not pulled back inside of the dilator. The dilator 28 and medical device 20 are dragged along the atrial septum 32 and positioned, for example against the fossa ovalis of the atrial septum using imaging of a marker 6 of functional tip 15. A variety of additional steps may be performed, such as measuring one or more properties of the target site, for example an electrogram or ECG (electrocardiogram) tracing and/or a pressure measurement, or delivering material to the target site, for example delivering a contrast agent through aperture(s) 7 and/or an open distal end. Such steps may facilitate the localization of the electrode 3 at the desired target site. In addition, tactile feedback provided by medical device 20 (radiofrequency perforation apparatus 20) is usable to facilitate positioning of the electrode 3 at the desired target site. The practitioner can visually monitor the position of functional tip 15 as it is advanced upwards into the heart and as it is dragged along the surface of the atrial septum 32 and positioned in the groove of the fossa ovalis.

With the electrosurgical device and the dilator positioned at the target site, energy is delivered from the energy source, through medical device 20 (radiofrequency perforation apparatus 20), to the target site. For example, if the radiofrequency perforation apparatus 20 is used, energy is delivered through the elongated member 2, to the electrode 3, and into the tissue at the target site. In some embodiments, the energy is delivered at a power of at least about 5 W at a voltage of at least about 75 V (peak-to-peak), and functions to vaporize cells in the vicinity of the electrode, thereby creating a void or perforation through the tissue at the target site. If the heart was approached via the inferior vena cava, as described hereinabove, the user applies force in the substantially cranial direction to the handle 1 of the electrosurgical device as energy is being delivered. The force is then transmitted from the handle to the distal portion 4 of the radiofrequency perforation apparatus 20, such that the distal portion 4 advances at least partially through the perforation. In these embodiments, when the distal portion 4 has passed through the target tissue, that is, when it has reached the left atrium, energy delivery is stopped. In some embodiments, the step of delivering energy occurs over a period of between about 1 s and about 5 s.

Some embodiments of methods of using the disclosed medical device comprise using a medical device 20 with a functional tip 15 that can be seen inside a substantially radiopaque dilator. Functional tip 15 includes a tip marker 6 with sufficient radiopacity that it can be seen under fluoroscopy. Medical device 20 may be used with a radiopaque dilator that can also be seen under fluoroscopy but that allows tip marker 6 to be seen within it. Substantially most, or all, of the dilator can be radiopaque, or just a distal portion of it. The use of tip maker 6 with such a compatible dilator can allow a physician to position functional tip 15 relative to the end of the dilator. For example, a physician could ensure that the tip of medical device 20 only protrudes out of the dilator 28 at the desired point in time. When performing a transseptal procedure using fluoroscopy, the radiopaque dilator can be positioned against the septum prior to crossing and the physician can maintain the tip of medical device within the dilatator. Since functional tip 15 can be seen inside of the dilator 28, it can be positioned just inside of the dilator tip immediately prior to attempting the transseptal crossing. It is only when the physician chooses to attempt to the crossing that an electrode 3 of a radiofrequency perforation apparatus 20 need be extended from the dilator. The physician can avoid having functional tip 15 accidentally extend beyond the end of the dilator before it is necessary.

It is also possible that the radiopaque-tipped radiofrequency perforation apparatus 20 and dilator 28 could be used with a catheter with a radiopaque marker at its tip to increase visibility and offer greater control to the physician.

As described herein above, medical devices are disclosed having improved visualization of a portion of the medical device insertable into a patient's body while minimizing obstruction of fluid flow through a lumen of the device and while minimizing an increase in the outer diameter of the device attributable to the feature providing improved visualization. The device can include, for example, an imaging marker distal to lumen openings (exit ports), or, where the device comprises a tube, such as a metallic tube, an imaging marker embedded into a wall of the tube. An alternative embodiment includes attaching a marker to the surface on the inside of a lumen of a medical device without substantially embedding the marker. Various alternative embodiments, methods and applications of using such devices are disclosed as well.

Additional details regarding the device and method not mentioned herein may be found in U.S. application Ser. No. 11/905,447, filed Oct. 1, 2007, U.S. application Ser. No. 13/113,326, filed May 23, 2007 U.S. application Ser. No. 11/265,304, filed Nov. 3, 2005 (now U.S. Pat. No. 7,947,040), U.S. application Ser. No. 10/666,301, filed Sep. 19, 2003 (now issued as U.S. Pat. No. 7,048,733), U.S. application Ser. No. 10/760,479, filed Jan. 21, 2004 (now issued as U.S. Pat. No. 7,270,662), U.S. application Ser. No. 10/666,288, filed Sep. 19, 2003, U.S. application Ser. No. 10/347,366, filed Jan. 21, 2003 (now issued as U.S. Pat. No. 7,112,197), U.S. provisional application Ser. No. 60/522,753, filed Nov. 3, 2004, and provisional applications Ser. No. 60/884,285, filed Jan. 10, 2007 and 60/827,452, filed Sep. 29, 2006. The contents of all above-named applications and patents are incorporated herein by reference in their entirety.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:
1. A medical device comprising:
an elongated member having a proximal end, a distal end, and a metal tube including an open distal end which is forward facing, the metal tube defining a lumen extend- ing substantially between the proximal end and the distal end of the elongated member, and the elongated member defining a side port from the lumen to an environment outside of the elongated member;

an electrode having a round shape and extending distally of the open distal end of the metal tube to define an atraumatic distal tip of the medical device, the electrode configured for delivering electrical energy, wherein the electrical energy is delivered to the electrode through the metal tube; and an imaging marker comprised of an electrically conductive metal associated with the elongated member at a marker location, the imaging marker being in electrical communication with the metal tube of the elongated member, the medical device configured such that, in use, a flow of fluid through the lumen to the side port is not substantially obstructed by the imaging marker, the imaging marker being located at the open distal end of the metal tube, wherein the imaging marker substantially occludes the lumen at the open distal end of the metal tube to prevent the flow of fluid in the lumen flowing past the marker location, and a portion of the imaging marker fills a portion of the lumen between the side port and the distal end of the elongated member and another portion of the imaging marker extends beyond the open distal end of the metal tube to outside of the lumen to define at least part of the electrode.

2. The medical device of claim 1, wherein the portion of the imaging marker which fills the portion of the lumen has a cylindrical shape and a solid cross-section.

3. The medical device of claim 1, wherein a first outer diameter of the medical device at the marker location is substantially equal to a second outer diameter of the medical device adjacent to the marker location.

4. The medical device of claim 1, further comprising a layer of insulation which covers the metal tube to distal of the side port and leaves a distal portion of the metal tube exposed, and the distal end of the elongated member comprises a functional tip which includes the imaging marker and the electrode, wherein the imaging marker is comprised of electrically conductive metal attached to the distal portion of the metal tube, and the electrode is comprised of a portion of the functional tip which extends beyond the layer of insulation.

5. The medical device of claim 4, wherein the imaging marker is comprised of metal which is more radiopaque than the metal tube.

6. The medical device of claim 2, the medical device further comprising a layer of insulation covering at least some of the elongated member and slightly overlapping a perimeter of the side port to thereby prevent the metal tube contacting a surrounding tissue while not covering a center of the side port to define an overlap which does not contact the metal tube.

7. The medical device of claim 6, wherein the side port is longitudinally elongated to provide for increased fluid flow.

8. The medical device of claim 1 wherein the imaging marker is an echogenic marker.

9. The medical device of claim 1 wherein the imaging marker is a marker visible under magnetic resonance imaging.

10. The medical device of claim 1, wherein the imaging marker is a radiopaque marker comprising a radiopaque material selected from the group consisting of platinum, iridium, gold, palladium, tungsten, and alloys thereof.

11. The medical device of claim 10, wherein the radiopaque material is comprised of about 90% platinum and about 10% iridium.

12. The medical device of claim 10, wherein the radiopaque material is comprised of about 92% platinum and about 8% tungsten.

13. The medical device of claim 1, further comprising a layer of electrical insulation along an outer surface of the metal tube.

14. The medical device of claim 1, wherein the metal tube is comprised of a proximal metal tube and a distal metal end member in electrical communication with the proximal metal tube.

15. The medical device of claim 14, wherein a layer of insulation covers at least some of the proximal metal tube and some of the distal metal end member, leaving a distal portion of the distal metal end member exposed to define at least a part of the electrode.

16. The medical device of claim 15, wherein the distal metal end member defines the open distal end of the metal tube and wherein the distal metal end member includes a functional tip which includes the electrode and the imaging marker, wherein the imaging marker is comprised of electrically conductive metal attached to a distal portion of the distal metal end member, and the electrode is comprised of the portion of the functional tip which extends beyond the layer of insulation.

17. The medical device of claim 16, wherein the layer of insulation which covers the metal tube extends beyond the metal tube to cover a portion of the functional tip which is proximal of the electrode.

18. The medical device of claim 4, wherein the imaging marker is substantially comprised of a radiopaque material.

19. A medical device comprising:

an elongated member having a metal tube defining a lumen extending through the elongated member to an open distal end, the elongated member having a side port extending from the lumen through a wall of the elongated member; and an imaging marker including an electrically conductive metal electrically coupled to the metal tube, the imaging marker coupled to the elongated member such that a first portion of the imaging marker is located in the lumen at a location between the side port and the open distal end such that the imaging marker substantially occludes the lumen and a second portion of the imaging marker extends beyond the open distal end of the metal tube, wherein the second portion of the imaging marker functions as an electrode and has a rounded distal end to define an atraumatic distal tip.

* * * * *